(12) United States Patent
So et al.

(10) Patent No.: US 11,827,674 B2
(45) Date of Patent: Nov. 28, 2023

(54) WET ADHESIVE PEPTIDES

(71) Applicant: US Department of the Navy, Arlington, VA (US)

(72) Inventors: Christopher R. So, Alexandria, VA (US); Kathryn J. Wahl, Alexandria, VA (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 0 days.

(21) Appl. No.: 18/172,867

(22) Filed: Feb. 22, 2023

(65) Prior Publication Data
US 2023/0234990 A1    Jul. 27, 2023

Related U.S. Application Data

(62) Division of application No. 17/163,733, filed on Feb. 1, 2021, now Pat. No. 11,608,360, which is a division of application No. 16/182,425, filed on Nov. 6, 2018, now Pat. No. 10,927,148.

(60) Provisional application No. 62/582,022, filed on Nov. 6, 2017.

(51) Int. Cl.
*C07K 14/00* (2006.01)
*B32B 37/12* (2006.01)
*C09J 5/04* (2006.01)
*C09J 189/00* (2006.01)

(52) U.S. Cl.
CPC ............ *C07K 14/001* (2013.01); *B32B 37/12* (2013.01); *C09J 5/04* (2013.01); *C09J 189/00* (2013.01); *C09J 2489/00* (2013.01)

(58) Field of Classification Search
CPC ...... C07K 14/001; C07K 14/00; B32B 37/12; C09J 5/04; C09J 189/00; C09J 2489/00
See application file for complete search history.

(56) References Cited

U.S. PATENT DOCUMENTS

| | | | | |
|---|---|---|---|---|
| 6,551,795 B1 * | 4/2003 | Rubenfield | ............ | C07K 14/21 435/6.15 |
| 7,319,142 B1 * | 1/2008 | Goldman | ............... | C07K 14/24 536/23.1 |
| 7,745,391 B2 * | 6/2010 | Mintz | ..................... | A61P 37/00 514/19.3 |
| 7,867,704 B2 * | 1/2011 | Kapur | .................... | C12Q 1/689 435/6.15 |
| 8,183,436 B2 * | 5/2012 | Alexandrov | ......... | C07K 14/415 435/320.1 |
| 8,343,764 B2 * | 1/2013 | Abad | ................. | C12N 15/8241 800/298 |
| 10,466,245 B2 * | 11/2019 | Sutton | .................... | C12Q 1/485 |

FOREIGN PATENT DOCUMENTS

WO    WO-2007117444 A2 * 10/2007    ........... C12N 15/111

* cited by examiner

*Primary Examiner* — Julie Ha
(74) *Attorney, Agent, or Firm* — US Naval Research Laboratory; Roy Roberts

(57) ABSTRACT

Peptides that form adhesive bonds, even in aqueous and/or saline environments, are disclosed. When aggregated, the peptides may be used in methods for producing hydrogels and/or adhesive materials. Synthetic peptide analogs are provided that are designed based on protein sequences found in barnacle adhesive, and may optionally be augmented with chemistry from other organisms that secrete proteins that adhere to substrates. The peptides may be used, for example, in biomedical and aqueous applications. Methods of using the aggregated peptides as adhesives are also provided.

5 Claims, 11 Drawing Sheets
Specification includes a Sequence Listing.

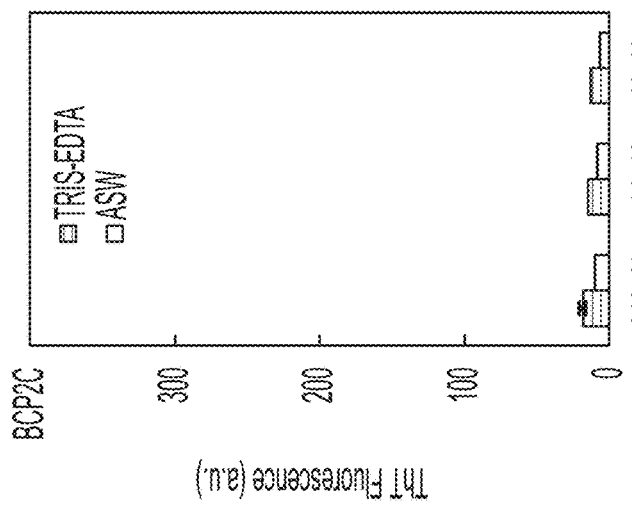
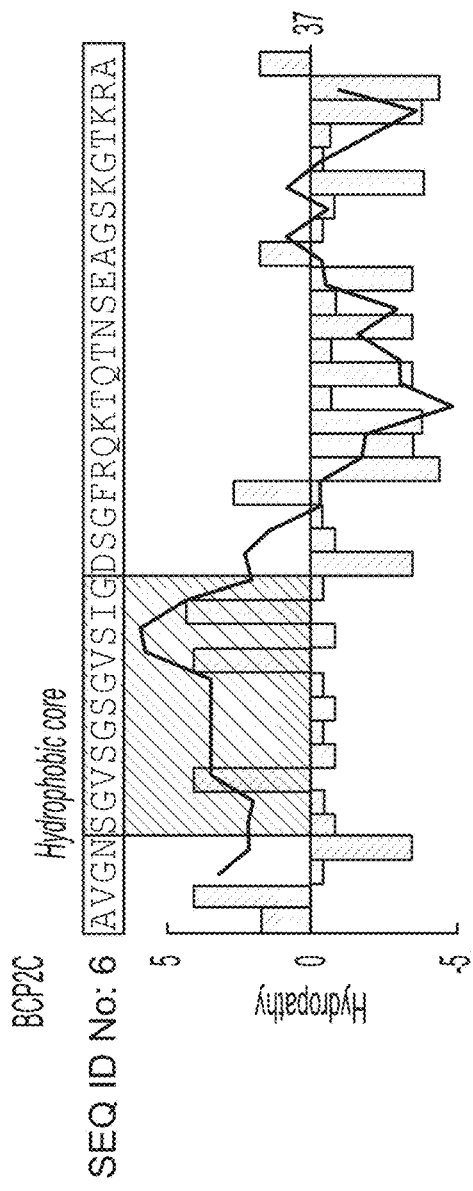
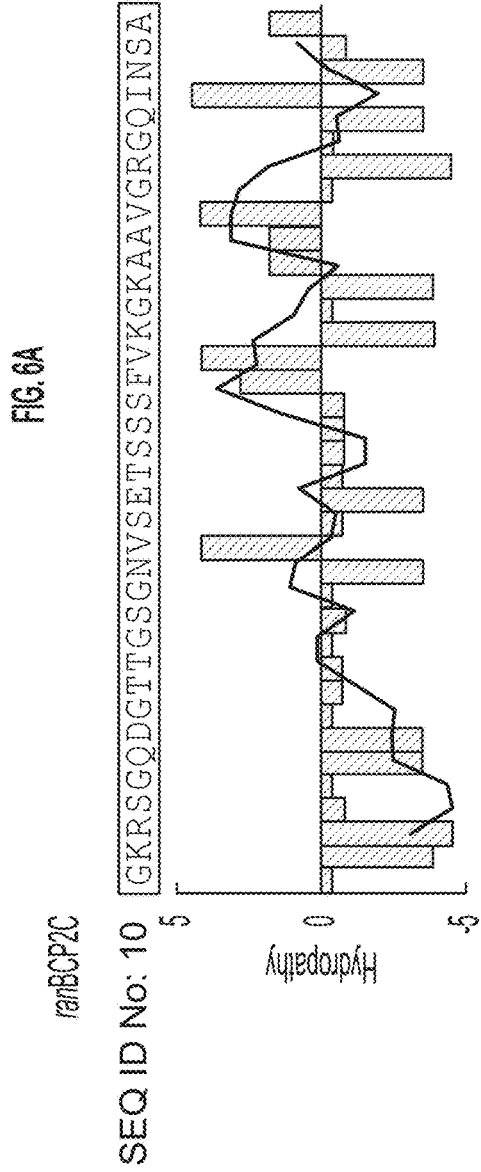
FIG. 6A
FIG. 6B
FIG. 6C

| Peptide | AU | Normalized |
|---|---|---|
| BCP2C | 0.3 | 0.89 |
| BCP2 | 0.1 | 0.28 |
| BCP1C | 0.34 | 1 |
| mutBCP1 | 0.05 | 0.15 | ns: adhesion, durability, bac-
WET ADHESIVE PEPTIDES

CROSS-REFERENCE TO RELATED APPLICATIONS

This application is a division of U.S. patent application Ser. No. 17/163,733 filed on Feb. 1, 2021 which itself is a is a division of U.S. patent application Ser. No. 16/182,425 filed on Nov. 6, 2018 (now U.S. Pat. No. 10,927,148), which in turn claims priority to U.S. Provisional Patent Application No. 62/582,022 filed on Nov. 6, 2017, the entirety of each of which is incorporated herein by reference.

SEQUENCE LISTING

This application contains a Sequence Listing, which has been submitted electronically in as a Sequence Listing XML, having the file name "107334US4-sequences.xml" and created on Feb. 22, 2023 with a file size of 92,356 bytes and is hereby incorporated by reference in its entirety.

FIELD OF THE DISCLOSURE

The invention relates to peptides that form adhesive bonds, even in aqueous and/or saline environments. When aggregated, the peptides may be used in methods for producing hydrogels and/or adhesive materials. Synthetic peptide analogs are provided that are designed based on protein sequences found in barnacle adhesive, and may optionally be augmented with chemistry from other organisms that secrete proteins that adhere to substrates. The peptides may be used, for example, in biomedical and aqueous applications. Methods of using the aggregated peptides as adhesives are also provided.

BACKGROUND OF THE INVENTION

Smart materials, wherein chemistry and material properties respond to environmental cues, are beneficial in applications where materials must be formed upon delivery, e.g., at a bonding surface or a wound site. In contrast to covalently bound materials such as cyanoacrylates, these materials can reversibly undergo phase transitions at ambient temperatures in response to external chemical or mechanical cues.

Fibrous biomaterials such as biological amyloids are of particular interest due to their high degree of order and unified molecular structure. They have become a desirable class of biomaterials where properties of a simple primary sequence can scale across molecular, nano-, meso-, and macroscopic distances. Knowles, et al. recently demonstrated these materials can be processed to form ordered bulk films with moduli of 5-7 GPa, rivaling films made from rigid carbon nanotubes, and consistent with the modulus of a single amyloid nanofiber (Knowles, T. P. J., et al., *J. Nature Nanotechnology* 2011, 6, 469).

X-ray diffraction and molecular modeling indicate that most natural amyloid materials are composed of crystalline β-sheets. The pattern of amino acids in these structures allows the placement of chemical species with high spatial precision solely through a primary letter sequence. For example, peptides with an alternating leucine (L) sequence motif will form micron-long nanofibers in which X side chains are displayed while leucine groups are buried (Rufo, C. M., et al., *Nat Chem* 2014, 6, 303). Thus, properties at the macroscopic length-scale are determined by a distinct sequence-structure relationship, forming tightly folded beta sheet structures that both maintain a strong network of fibers and promote display of functional amino acid side chain chemistries. Though much work has been done to understand the hierarchy of physical properties in templated and self-assembled amyloid materials, imparting chemistry and multiple functions to these materials presents an unexplored frontier.

Despite intense efforts to develop temperature, pH and ionic strength triggers in protein and peptide materials, copolymerization of two or more distinct components as a smart material trigger has received little attention. For example, peptides designed with hairpin turns fold into a precursor structure that is favorable for fiber assembly when specific side-chains are deprotonated under basic conditions (Schneider, J. P., et al., *J Am Chem Soc* 2002, 124, 15030; Yucel, T., et al., *Macromolecules* 2008, 41, 5763). Other synthetic proteins are based on elastins (Brennan, M. J., et al., *Biomaterials* 2017, 124, 116; McMillan, R. A., et al., *Macromolecules* 2000, 33, 4809; Huang, L., et al., *Macromolecules* 2000, 33, 2989), which are triggered by exploiting a glass transition temperature dependent on the arrangement of the sequence.

Current synthetic materials rely on temperature, pH and ionic strength to form bulk gels, while many natural systems achieve transitions without external cues purely by recognition between proteins (So, C. R., et al., *Sci Rep* 2016, 6, 36219; Barnhart, M. M., et al., *Annu Rev Microbiol* 2006, 60, 131; Chapman, M. R., et al., *Science* 2002, 295, 851; Hammer, N. D., et al., *P Natl Acad Sci USA* 2007, 104, 12494; Cheung, P. J., et al., *Mar Biol* 1977, 43, 157; Kamino, K., *Biofouling* 2013, 29, 735). Engineered systems are largely homopolymers, formed from a single monomer, limiting the additional functionality that could be brought about by the co-polymerization of two or more components. These sequences also involve more than 50% of the chain chemistry in the assembly and formation of fibers, providing little room for incorporation of other functionalities.

In contrast to marine organisms that use glues to fabricate protective shelters (e.g., sand-castle worm tubes, case-maker fly larva retreats, and amphipod tubes) or tie themselves to rocks, (e.g., mussel byssus threads) adult barnacles produce their adhesive interface in a sequential process hidden under their base as a part of their normal growth cycle. The recent finding that barnacle adhesive is nanostructured and held together as an amyloid-like material further distinguishes it from archetypal marine adhesives processed into solid foams or spun threads. The permanent adhesive produced by adult barnacles is held together by tightly folded proteins that form amyloid-like materials unique among marine foulants. The adhesive is polymerized from protein subunits that form a micron-thick layer of ordered nanofibers and function as a permanent wet adhesive.

Barnacles use hydrogen bonds to tightly fold their adhesive proteins and display side chains to achieve enhanced mechanical strength, protein bundling, and co-localized reactive chemistries. The polymerization of barnacle glue occurs through these molecular interactions, and the resulting adhesive is a meshwork of nanoscale fibers. Proteomic surveys suggests that barnacle glue functions by displaying adhesive chemistries through small and flexible side-chains, folded in a manner similar to adhesive silks used by spiders and insects (So, C. R., et al., *Sci Rep* 2016, 6, 36219). These fibers are complex co-polymers, formed from the specific interactions between more than 20 different protein components. Their well-defined, modular nature permits barnacle adhesive to serve many purposes: adhesion, durability, bacterial resistance, and even potent enzymatic activity (So, C.

R., et al., *ACS Appl Mater Interfaces* 2017, 9, 11493). Moreover, the absence of cellular processes at the attachment surface suggests that delivery, assembly, and displayed chemistry of adhesive nanomaterials are governed by the physical properties of patterned non-charged amino acids.

Hydrogels and adhesives have been developed based on various peptides. For example, U.S. Patent Appl. Publ. No. 2017/0015885 by Liu et al. ("Liu") is directed to protein-based adhesives. An elastin-like polypeptide is provided.

U.S. Pat. No. 7,884,185 to Schneider et al. ("Schneider") is directed to hydrogels and methods of making and using such hydrogels. Schneider provides hydrogels that may be formed by the self-assembly of peptides in solution. Such self-assembly may be brought about by a change in one or more characteristics of the solution. Characteristics of the solution that may be changed include pH, ionic strength, temperature, and concentration of one or more specific ions. The hydrogels described by Schneider may be disassembled by changing one or more characteristic of the hydrogel.

U.S. Pat. No. 9,228,009 to Hartgerink et al. ("Hartgerink") is directed to collagen, and more particularly compositions and methods related to collagen-mimetic peptides. Hartgerink provides a collagen-mimetic peptide and peptide systems.

U.S. Pat. No. 9,493,513 to Mehmet et al. ("Mehmet") is directed to polypeptides that bind to inorganic solid surfaces, structures comprising such polypeptides, and methods of making such structures.

However, there remains a need in the art for peptide-derived polymers and hydrogels, particularly those that may be used as adhesives in aqueous environments.

SUMMARY OF THE INVENTION

The invention described herein, including the various aspects and/or embodiments thereof, meets the unmet needs of the art, as well as others, by providing peptides that form adhesive bonds, even in aqueous and/or saline environments. When aggregated, the peptides may be used in methods for producing hydrogels and/or adhesive materials. Synthetic peptide analogs are provided that are designed based on protein sequences found in barnacle adhesive, and may optionally be augmented with chemistry from other organisms that secrete proteins that adhere to substrates. The peptides may be used, for example, in biomedical and aqueous applications. Methods of using the aggregated peptides as adhesives are also provided.

In one aspect of the invention, a peptide is provided that has an amino acid sequence of any one of SEQ ID Nos:1-8.

In another aspect of the invention, a peptide is provided that has an amino acid sequence including one of the conserved sequence patterns of SEQ ID Nos:11-20.

Peptides can be further tailored to include chemistries that enhance adhesive properties, through addition of amino acids or modification of existing amino acids.

According to a further aspect of the invention, a method for forming a wet adhesive includes providing a first surface; covering at least a portion of the first surface with a first peptide; and introducing a second peptide in contact with the first peptide. Upon contact of the first peptide with the second peptide, the first peptide and second peptide self-assemble into a solid adhesive material.

Other features and advantages of the present invention will become apparent to those skilled in the art upon examination of the following or upon learning by practice of the invention.

BRIEF DESCRIPTION OF THE DRAWINGS

FIG. 2A shows a glue shaving from *Amphibalanus amphitrite* exposed to ThT (10 mM) for <15 min and imaged via a fluorescence microscope, with an inset untreated glue shaving. FIG. 2B shows that ThT increases fluorescence intensity upon binding to BCP2C fibrils present in solution. FIG. 2C shows that synthetic barnacle cement peptides have varied activity over a 300 hour period. FIG. 2D shows that active BCP1C/2/2C in Tris-EDTA and ASW undergo a growth phase, reaching a steady state ThT fluorescence. FIG. 2E shows the estimated aggregation onset (Lag time ($Tin_g$)).

FIG. 4A shows, from top to bottom, BCP2 with only a simple domain maintains similar modes but does not display the prominent feature at 1698 $cm^{-1}$. BCP2C spectrum showing three additional modes at 1525 $cm^{-1}$ (Amide II), 1661 $cm^{-1}$ and 1698 $cm^{-1}$ (anti-parallel turn). mutBCP1 amide region similar to BCP2 with a main peak at 1626 $cm^{-1}$ and a shoulder at 1656 $cm^{-1}$ with no modes near 1700 $cm^{-1}$. Bottom, BCP1C spectrum showing similar modes as the BCP2C spectrum including the prominent shoulder at 1698 $cm^{-1}$. FIG. 4B shows peak deconvolution of amide modes from FIG. 4A, showing a prominent peak at 1698 $cm^{-1}$, using five element Lorentzian fit for BCP2/2C/1C and three element fitting for mutBCP1.

FIGS. 5C-5E show representative ThT fluorescence aggregation curves of seed activation or acceleration. Fit of sigmoidal least squares regression trace (solid black line) shown with data points. Values of lag time are obtained from this fit. FIG. 5C shows that dormant BCP3C is activated in the presence of preformed BCP2C seed fibrils in Tris-EDTA from no measured onset to 17 h. FIG. 5D shows the preformed BCP2C radically accelerated BCP2 aggregation onset from 30 h to <2 h. FIG. 5E shows that dormant BCP1 is activated in the presence of preformed BCP1C seed fibrils in ASW from no onset to 30 h.

FIGS. 6A-6C show that randomization of BCP2C modifies peptide activity and aggregation by disruption of distinctive hydrophobic core sequence. FIG. 6A is a schematic representation of BCP2C that demonstrates the simple and charged domains, as well as an identified hydrophobic core in both the sequence and hydropathy. FIG. 6B shows the amino acid sequence of BCP2C randomized (ranBCP2C) with corresponding hydropathy. In both FIG. 6A and FIG. 6B, a 5-window moving average of hydropathy using the Kyte and Doolittle scale is overlaid as a line with a scale of −3.5 to 1.5, where hydrophilic residues have a hydropathy index below zero and hydrophobic resides above zero. The grand average of hydropathy (GRAVY) value of both BCP2C and ranBCP2C was −0.7378. FIG. 6C shows that ranBCP2C inhibits self-assembly (no activity) and polymerization after 300 hours.

FIGS. 7A-7C show the incorporation of BCP peptides in newly deposited barnacle cement. FIG. 7A shows re-settled barnacles grown on nitrocellulose membranes (NC) for 72 hours. FIG. 7B shows a Western blot analysis of barnacles peeled from NC, where the left panel represents a membrane incubated with HRP conjugated anti-rabbit antibodies. The center panel and right hand side panels are independent re-settled barnacles blotted against α-CP43 and α-CP19, respectively. FIG. 7C shows NC-bound barnacle cement incubated with (from left to right) FITC labeled BCP4 (positive response), TRITC labeled BCP2C (positive response) or TRITC labeled poly-lysine peptide (negative response).

DETAILED DESCRIPTION OF EMBODIMENTS OF THE INVENTION

Figure 1:
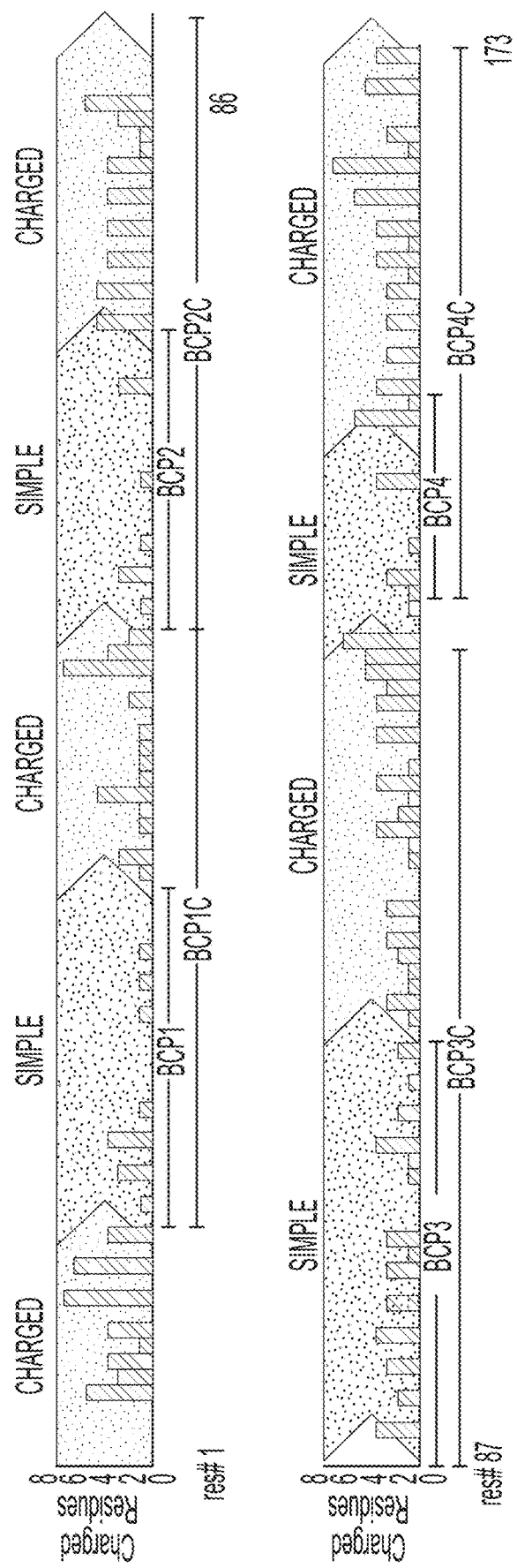
FIG. 1 shows a plot of charged residues per sequence for a multiple sequence alignment of five barnacle cement proteins, which show 10 instances of a 19 kD motif repeated along full length protein sequences.

The invention described herein, including the various aspects and/or embodiments thereof, meets the unmet needs of the art, as well as others, by providing peptides that form adhesive bonds, even in aqueous and/or saline environments. When aggregated, the peptides may be used in methods for producing hydrogels and/or adhesive materials, including materials that exhibit adhesive properties underwater. Synthetic peptide analogs are provided that are designed based on protein sequences found in barnacle adhesive, and may optionally be augmented with chemistry from other organisms that secrete proteins that adhere to substrates. The peptides may be used, for example, in biomedical and aqueous applications. Methods of using the aggregated peptides as adhesives are also provided.

In the context of the present invention, barnacles include organisms of the order Sessilia, preferably barnacles of family Balanidae (particularly barnacles of the genera *Balanus, Fistulobalanus,* and *Amphibalanus*), and family Archaeobalanidae (particularly barnacles of the genus *Semibalanus*). The peptides of the invention may be derived from the cement of *Amphibalanus amphitrite,* a species of acorn barnacle. These sequences exhibit a unique dual nature that is both an ordered silk-like structure and a chemical adhesive, as non-charged segments demonstrate homology (e-value of ca. 10-30) with adhesive silk motifs. Well-defined sequence domains, as observed in barnacles, provide the present invention with the ability to exert independent control over structural and adhesive properties. In some aspects of the invention, this can be achieved by utilizing a sequence of approximately 35-50 residues, preferably approximately 35-40 residues.

A family of barnacle proteins rich in distinct stretches of alternating charged and non-charged linear sequence has been identified in accordance with the invention. These stretches are referred to as "charged" domains, where not more than 50% of the sequence is comprised of charged amino acids, and not more than 50% of the sequence is comprised of non-charged amino acids. Recombinant protein and peptide sequences are designed using the patterned domains identified in the natural adhesive that contain non-charged and charged sequence [Gly/Ala/Thr/Ser/Val-X], where X corresponds to charged amino acids. These sequences are referred to as barnacle cement derived peptides (BCPs). Charged amino acids relevant to the invention are Arginine (R), Lysine (K), Aspartic acid (D), Glutamic acid (E), Histidine (H). Non-charged amino acids relevant to the invention are Serine (S), Threonine (T), Glycine (G), Alanine (A), Leucine (L), Isoleucine (I), Valine (V). Charged domains alternate with stretches of non-charged amino acids, referred to as "simple" domains. Simple domains are comprised of mostly non-charged amino acids as defined above, with not more than 20% charged amino acid content. The role of simple and charged domains in forming fibrillar materials has also been identified. These sequences exert specific control over timing, structure and morphology of fibril formation.

While most BCPs remain dormant, a core segment demonstrates rapid polymerization as well as an ability to template other peptides, even if they have no intrinsic propensity for self-assembly. Without wishing to be bound by theory, it is believed that the patterned charge domains assemble dormant peptides through a unique anti-parallel beta sheet structure. While charged domains favor an anti-parallel structure, BCPs without charged domains switch fibril assembly to favor simpler parallel beta sheet aggregates. In addition to activation, charged domains add persistence length to resulting nanofibers, mimicking fibrils observed in the natural adhesive, while segments without such domains only form short, branched aggregates. The specific activation of dormant peptides through recognition of structured amyloid-like templates is similar to mechanisms of biological recognition between proteins, and permits control over physical mechanisms including adhesive delivery, activation, and curing.

Peptides.

The invention provides peptide sequences that can be polymerized to form hydrogels and adhesives. The sequences of the invention contain a highly conserved pattern alternating between 20-25 peptide-long, "simple" domains having a greater proportion (80-100%) of non-charged amino acids (i.e., Gly, Ser, Thr, Ala, Val, Ile residues), and 10-25 peptide-long, "charged" domains having a greater proportion (40-60%) of charged (i.e., Arg/Lys/Asp/Glu/His residues) intermixed with not more than 50% non-charged amino acids.

The sequences of the invention form distinct patterns that result in structural fibers. Five core proteins identified in the cement of barnacles (Accession ID numbers AKZ20819.1, AQA26371.1, AQA26372.1, AQA26373.1, and AQA26376.1) each comprise from 9 to 25 of these short alternating simple and charged domains, underscoring their role as a major design element for marine adhesion. The peptides of the invention may therefore be provided as short sequences including a simple domain and a charged domain. These simple and charged domains may be repeated to form longer synthetic peptides incorporating from 6-100 domains, preferably from 8-60 domains, more preferably from 10-30 domains. The same simple and charged domains may be repeated as a pattern throughout the synthetic peptides, or several different simple and charged domains of the invention may be used to form the synthetic peptides. The simple and charged domains may be provided without any intervening amino acids between each domain, or intervals of several amino acids may separate the domains.

These simple domain and charged domain sequence patterns are conserved among *Amphibalanus amphitrite* barnacle cement proteins. As shown in FIG. 1, charged and simple domains were identified based on a multiple sequence alignment of barnacle cement proteins from *A. amphitrite*, specifically, by alignment of the proteins corresponding to Accession ID numbers AKZ20819.1, AQA26371.1, AQA26372.1, AQA26373.1, and AQA26376.1. A 19 kD domain was identified in Accession ID No. AKZ20819.1 that spanned amino acids 33-199, which was found to correspond to similar domains in Accession ID numbers AQA26371.1 (a first domain was identified that spanned amino acids 31-204, and a second domain was identified that spanned amino acids 205-368); AQA26372.1 (a first domain was identified that spanned amino acids 55-220, and a second domain was identified that spanned amino acids 228-393), AQA26373.1 (a first domain was identified that spanned amino acids 40-214, and a second domain was identified that spanned amino acids 254-442), and AQA26376.1 (three domains were identified: a first domain that spanned amino acids 21-182, a second domain that spanned amino acids 195-360, and a third domain that spanned amino acids 385-518). The charged residues are plotted in the domain map shown in FIG. 1.

These identified sequence patterns were used to design a set of peptides that contain conserved, non-charged (termed, "simple") domains along with their neighboring patterned, charged (termed, "charged") domains. These synthetic mimics are referred to as barnacle cement peptides (BCPs).

The simple domains include, but are not limited to:

BCP1
(SEQ ID NO: 1)
QTGYTRGGAAVSSTGATQGAGS

BCP2
(SEQ ID NO: 2)
AVGNSGVSGSGVSIGDSGFRQKTQT

BCP3
(SEQ ID NO: 3)
TGTQGKGITSGEAVANQKAGAEGG

BCP4
(SEQ ID NO: 4)
GTSSSGHKASSSGPGRFITSN

The simple domains further include peptides having 90% or greater identity to these sequences, preferably 95% or greater identity to these sequences, more preferably 98% or greater identity to these sequences.

The combined simple and charged domains include, but are not limited to:

BCP1C
(SEQ ID NO: 5)
QTGYTRGGAAVSSTGATQGAGS LDLAIDGPGGFKARSK

BCP2C
(SEQ ID NO: 6)
AVGNSGVSGSGVSIGDSGFRQKTQT NSEAGSKGTKRA

BCP3C
(SEQ ID NO: 7)
TGTQGKGITSGEAVANQKAGAEGG AQRVEAVKYVESDGKNLYKVEKVD

BCP4C
(SEQ ID NO: 8)
GTSSSGHKASSSGPGRFITSN EVGTEIKLTTPELD

The combined simple and charged domains further include peptides having 90% or greater identity to these sequences, preferably 95% or greater identity to these sequences, more preferably 98% or greater identity to these sequences.

In addition to these synthetic peptides, a mutant form of BCP1 and a randomized form of BCP2C were also generated in order to compare their properties with those of the sequences set forth above. These peptides include:

mutBCP1
(SEQ ID NO: 9)
QTGYTRGGAAVSSTGATQ(G→C)AGS ranBCP2C
(SEQ ID NO: 10)
GKRSGQDGTTGSGNVSETSSSFVKGKAAVGRGQINSA Also within the scope of the invention are sequences that incorporate conserved patterns along the length of the 19 kD homologous sequence. These peptide patterns include:

(SEQ ID NO: 11)
[QxGxTGGAxVSxxGxTQGxGS]$_{simple}$ +

[patterned charged domain]$_{charged}$ (SEQ ID NO: 12)
[AVGNSGVSGxGxSxGxGxFxQ]$_{simple}$ +

[patterned charged domain]$_{charged}$ (SEQ ID NO: 13)
[VTxTxGxGxTxGxAxQKAGANGG]$_{simple}$ +

[patterned charged domain]$_{charged}$

-continued (SEQ ID NO: 14)
[AxSSSGHxASSxGxGxFxVxNxxxTExK]$_{simple}$ +

[patterned charged domain]$_{charged}$ (SEQ ID NO: 15)
[TxTxGxGxTGxAxxxQKAGANGG]$_{simple}$ +

[patterned charged domain]$_{charged}$ (SEQ ID NO: 16)
[xTSSSGHxASSxGxGxFxVxN]$_{simple}$ +

[patterned charged domain]$_{charged}$

In some aspects of the invention, the conserved peptide patterns may be further characterized as follows:

(SEQ ID NO: 17)
[QxGxTxGGAxVSxxGxTQGxGS]$_{simple}$ +

[xDxxxDGGGGDKxRxK]$_{charged}$ (SEQ ID NO: 18)
[AVGNSGVSGNGxSxGxGxFxQ]$_{simple}$ +

[xxExxxKxxKRx]$_{charged}$ (SEQ ID NO: 19)
[VxTYTxGxGxTxGxAxxxxQKAGANGG]$_{simple}$ +

[xxRxExxKxxExDxKxxxKxEKxD]$_{charged}$ (SEQ ID NO: 20)
[AxSSSGHxASSxGxGxFxVxNxxxTExK]$_{simple}$ +

[ExxxExKxxxxExD]$_{charged}$

In each of these conserved peptide patterns, the [x] denotes a permissive site that is not conserved. In some aspects of the invention, each instance of "x" independently corresponds to an amino acid selected from the group consisting of Gly, Ser, Thr, Ala, Val, Ile, Lys, Arg, Glu, Asp, Asn, Gln residues. Within a given peptide, each x may be the same or different. Preferably, x is an amino acid selected from the group consisting of Gly, Ser, Thr, Ala, Val, Ile.

For example, the patterned charged domain used in the peptide pattern for BCP1C may encompass the following peptides, in which [x] corresponds to Ala, Ser, Gly, or Thr:

(SEQ ID NO: 21)
QAGATAGGAAVSAAGATQGAGS ADAAADGGGGDKARAK (SEQ ID NO: 22)
QSGSTSGGASVSSSGSTQGSGS SDSSSDGGGGDKSRSK (SEQ ID NO: 23)
QGGGTGGGAGVSGGGGTQGGGS GDGGGDGGGGDKGRGK (SEQ ID NO: 24)
QTGTTTGGATVSTTGTTQGTGS TDTTTDGGGGDKTRTK

However, the invention is not limited to these particular peptides, and encompasses peptides in which [x] corresponds to a residue selected from Gly, Ser, Thr, Ala, Val, Ile, Lys, Arg, Glu, Asp, Asn, or Gln, where each instance of [x] may be the same or different.

For example, the patterned charged domain used in the peptide pattern for BCP2C may encompass the following peptides, in which [x] corresponds to Ala, Ser, Gly, or Thr:

(SEQ ID NO: 25)
AVGNSGVSGAGASAGAGAFAQ AAEAAAKAAKRA (SEQ ID NO: 26)
AVGNSGVSGSGSSSGSGSFSQ SSESSSKSSKRS (SEQ ID NO: 27)
AVGNSGVSGGGGSGGGGFGQ GGEGGGKGGKRG (SEQ ID NO: 28)
AVGNSGVSGTGTSTGTGTFTQ TTETTTKTTKRT

However, the invention is not limited to these particular peptides, and encompasses peptides in which [x] corresponds to a residue selected from Gly, Ser, Thr, Ala, Val, Ile, Lys, Arg, Glu, Asp, Asn, or Gln, where each instance of [x] may be the same or different.

For example, the patterned charged domain used in the peptide pattern for BCP3C may encompass the following peptides, in which [x] corresponds to Ala, Ser, Gly, or Thr:

(SEQ ID NO: 29)
VATATAGAGATAGAAAAAQKAGANGG

AARAEAAKAAEADAKAAAKAEKAD (SEQ ID NO: 30)
VSTSTSGSGSTSGSASSSQKAGANGG

SSRSESSKSSESDSKSSSKSEKSD (SEQ ID NO: 31)
VGTGTGGGGGTGGGAGGGQKAGANGG

GGRGEGGKGGEGDGKGGGKGEKGD (SEQ ID NO: 32)
VTTTTTGTGTTTGTATTTQKAGANGG

TTRTETTKTTETDTKTTTKTEKTD

However, the invention is not limited to these particular peptides, and encompasses peptides in which [x] corresponds to a residue selected from Gly, Ser, Thr, Ala, Val, Ile, Lys, Arg, Glu, Asp, Asn, or Gln, where each instance of [x] may be the same or different.

For example, the patterned charged domain used in the peptide pattern for BCP4C may encompass the following peptides, in which [x] corresponds to Ala, Ser, Gly, or Thr:

(SEQ ID NO: 33)
AASSSGHAASSAGAGAFAVANAAATEAK EAAAEAKAAAAEAD (SEQ ID NO: 34)
ASSSSGHSASSSGSGSFSVSNSSSTESK ESSSESKSSSSESD (SEQ ID NO: 35)
AGSSSGHGASSGGGGFGVGNGGGTEGK EGGGEGKGGGGEGD (SEQ ID NO: 36)
ATSSSGHTASSTGTGTFTVTNTTTTETK ETTTETKTTTTETD

However, the invention is not limited to these particular peptides, and encompasses peptides in which [x] corresponds to a residue selected from Gly, Ser, Thr, Ala, Val, Ile, Lys, Arg, Glu, Asp, Asn, or Gln, where each instance of [x] may be the same or different.

The peptides of the invention may exhibit varying levels of fibril formation, and different sets of peptides may be created to tailor the extent of fibril formation and the rate of fibril formation. Preferably, one set of peptides is limited to the simple domains (i.e., BCP1, BCP2, BCP3, and BCP4) while the other set of peptides includes both the simple domain and an additional charged domain incorporating G-x, S-x, and/or V-x sequence patterns (where x is as defined above, and designates charged residues). Examples of charged domains include those found in the patterned domains incorporated into the peptides BCP1C, BCP2C, BCP3C, and BCP4C.

The peptides of the invention may be provided individually, or as combinations of two or more of the peptides of the invention. The peptides may be provided together or separated into sets of peptides. The first peptide or first set of peptides may be dormant (i.e., they may not self-assemble into fibrils), and may only assemble into fibrils on contact with a second peptide or second set of peptides, where the second peptide or second set of peptides templates the first peptide or first set of peptides to cause fibril formation. The first and second peptides may self-assemble into fibrils that result in adhesion when applied to surfaces. In some aspects of the invention, the first set of peptides includes peptides having an amino acid sequence as set forth in any one of SEQ ID Nos:1-8 and 11-20. In further aspects of the invention, the second set of peptides is selected from peptides having an amino acid sequence based on those set forth for BCP2 and BCP2C (SEQ ID Nos:2, 6, 12, and 18).

The peptides of the invention may further be chemically altered by introducing new amino acids to the sequence (e.g., at the N and/or C terminal, or between one or more repetitions of the simple and charged domains of the invention) or modifying existing amino acids to augment adhesive properties underwater. This can be done by replacing, for example, non-charged sequence positions with tyrosine residues and performing oxidation of the side chain to dihydroxyphenylalanine (DOPA). DOPA has been shown to displace water and form bidentate interactions with inorganic surfaces. Alternatively, serines in the existing sequence can be modified by chemical or biochemical means to display phosphate groups, which mediate wet adhesion through divalent ions and ionic interactions with surfaces. Serines can also be modified with long or short chain polysaccharides, which promote adhesive interactions with inorganic surfaces. These modifications all enhance chemical adhesion of the formed material in underwater environments.

The peptides may be screened using high throughput tools for amyloid characterization including fluorometric Thioflavin T (ThT) experiments, fluorescence microscopy, atomic force microscopy (AFM), and Fourier Transform Infrared Spectroscopy (FTIR) of formed materials. (See, e.g., FIGS. 2A-2E and 3A-3C.) Certain simple peptide motifs aggregate and form fibrils, while the addition of one or more neighboring charged patterns template microns-long fibril materials of higher order. The addition of charged domains can template other sequences with no ability to form fibrils on their own, rendering them able to form fibrils as a result. This templating capability of certain peptides of the invention provides a strategy for timed polymerization in the delivery and curing of an adhesive in an aqueous environment.

The peptides according to the invention may be chemically-produced using known methods of peptide synthesis, for example by solid phase synthesis. The peptides may also be produced using recombinant methods that rely upon introducing genes encoding the peptides of interest into a host organism that is suitable for production of the peptides, and the host organism transcribing and translating the genes. The genes may be introduced into a host organism via a vector, in particular an expression vector. The functional unit including a gene, an operably-linked promoter, and optionally other genetic elements are referred to as an "expression cassette."

Nucleotides that encode the peptides of the invention may be formed using methods which are generally known in the art, such as chemical synthesis or the polymerase chain reaction (PCR), in conjunction with standard molecular biology and/or protein synthesis techniques. For example, it is possible for those skilled in the art, on the basis of known DNA and/or amino acid sequences, to produce the corresponding nucleic acids and even complete genes.

The invention further provides prokaryotic or eukaryotic cells that have been transformed with nucleic acids that encode for peptides according to the invention.

Hydrogels and Adhesive Materials.

Adhesive materials in accordance with the invention preferably exhibit properties that include: (1) they exist as a liquid prior to bonding, and solidify at the site to be adhesively bonded; (2) the formed material spans two surfaces (i.e., a first surface and a second surface, which may have the same or different compositions); (3) the formed material provides enhanced cohesive bond strength by way of networked covalent or non-covalent polymer chemistries; and (4) the formed material displays chemistry capable of displacing water and forming chemical interactions with surfaces in aqueous environments. Preferred material systems of the invention exhibit all four of these properties simultaneously. Synthetic analogs to natural barnacle glue sequences can be tailored to display enhanced or shielded underwater adhesive interactions with surfaces. These non-natural peptides, used in wholly synthetic environments, are demonstrated to fulfill all criteria as an underwater adhesive material system as embodied in this invention.

The peptides of the invention may be used to produce hydrogels that can be delivered as a liquid, and subsequently polymerized by recognition of BCP2/BCP2C and related peptides to form an adhesive gel. These peptides represent a new class of peptide hydrogel materials, where copolymerization occurs specifically between designed sequences to form heterogeneous smart gel materials.

The invention provides hydrogels that comprise networked barnacle-like protein fibers held together by organized hydrogen bonds exhibit high rigidity at low weight percentages, yet retain the ability to revert back to liquid form under mechanical shear. The hydrogels have the ability to be externally triggered into gelation, back to liquid form, and reassembled into a gel network. The ability for the inventive adhesive materials to be delivered to the bonding site as a liquid, and triggered to polymerize into a functional gel is based on non-covalent interactions and recognition between unique protein sequences.

Specific amino acid sequences found in barnacle cement proteins control material polymerization and curing underwater through specific intermolecular interactions and aggregation timescales, providing a means to localize adhesive formation. The short synthetic peptides of the invention mimic segments of smart adhesive gels from barnacles, and also demonstrate control over polymerization, where a unique master sequence (i.e., BCP2/BCP2C and related peptides) induces fiber formation and gelation in dormant sequences. Lock-and-key recognition by synthetic bioinspired peptides is therefore a viable strategy for the delivery and formation of smart gel materials with adhesive properties. The control over polymerization and delivery of adhesive gels underwater using barnacle cement-mimicking peptides is beneficial for biomedical and marine adhesives, as well as applications that require environmentally-responsive hydrogel adhesives.

Formation of smart gels by sequence recognition and co-polymerization of designed peptide sequences into bulk barnacle cement-derived peptide materials allows the incorporation of multiple functions, including underwater adhesion, into a deliverable system. Incorporation of multiple components into a co-polymer via sequence recognition also allows control of component order found along composite fibers. This discovery sets barnacle-derived peptides apart from existing designed peptide-based materials. Imparting multiple chemical and biological functions to materials is currently a multistep process, requiring specific surface and protein linker chemistries as well as reactions that work only in dry environments. Marine organisms such as barnacles, on the other hand, produce a chemically-, biologically-, and mechanically-robust attachment to nearly any surface by depositing just one single layer of proteinaceous material. These robust materials are structured as a meshwork of ordered nanoscale fibers, formed in seawater, and survive years of harsh marine exposure. The synthetic peptides of the invention also achieve these benefits.

Adhesive compositions in accordance with the invention may be formed by incorporating the inventive peptides into a vehicle, such as an aqueous vehicle, along with one or more buffers, crowding agents such as polysaccharides (Ficoll®, GE Healthcare, Chicago, IL) and polyethylene glycol (PEG), glycerol, sea water or artificial sea water (Instant Ocean®, Instant Ocean Spectrum Brands, Blacksburg, VA), preservatives, or other additives as known to those skilled in the art.

Adhesive compositions in accordance with the invention may also be formed by incorporating the inventive peptides into a water immiscible vehicle, which may include one or more nonpolar solvents (including, but not limited to, dimethyl sulfoxide, dimethyl formamide, and dichloromethane), lipids, and oils, and optionally including additional crowding agents such as polysaccharides (Ficoll®) and polyethylene glycol (PEG), preservatives, or other additives as known to those skilled in the art.

The adhesives of the invention may be provided as a single solution, or as two separate solutions to be combined when the adhesive bond is formed. When provided as a single component, a shear force may be applied to the peptides of the invention in order to deliver the peptides to a surface being bonded. Once the shear force is removed and the peptides are in place on the surface, the peptides self-assemble into fibrils. When provided as a two-component system, a first peptide is applied to a surface being bonded, where the first peptide is not capable of self-assembly into fibrils. The application of the second peptide causes the first peptide to be templated, and results in self-assembly of the mixture of first and second peptides into fibrils.

Conventional adhesives may be replaced by the inventive peptides in order to provide adhesives capable of being used in environments that are moist or aqueous, including plant and animal tissues, freshwater structures and vehicles, and saltwater/marine structures and vehicles. In addition to being specifically adapted for use in aqueous environments, they are also suitable for use in applications where conventional adhesives are used. In additional aspects of the invention, the peptide-based adhesives of the invention may be used in conjunction with conventional adhesives.

Assays.

The invention also provides assays, which may be used by those skilled in the art to determine if a particular peptide is likely to have cementitious properties, or be useful as a hydrogel and/or adhesive. To establish experimental conditions that form fibers from designed mimics, assays are provided that are sensitive to ordered molecular structures. The assays have the ability to monitor growth kinetics for up to 96 simultaneous reactions spanning 48 hours, while maintaining a constant volume in the hundred-microliter range.

Figures 4A, 4B:
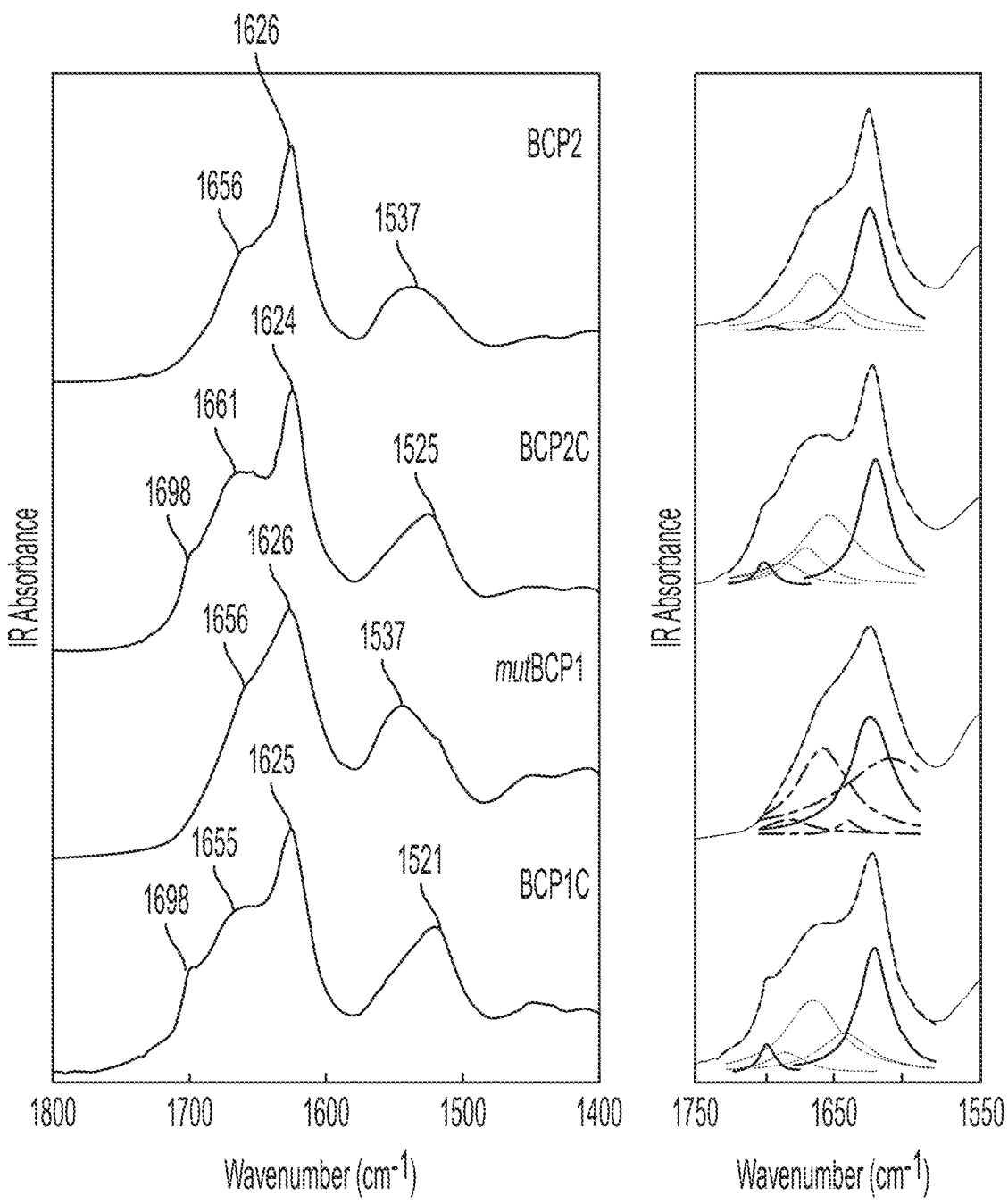
FIGS. 4A and 4B show amide regions from transmission FTIR of dried BCP materials on $CaF_2$ that displayed activity by ThT. Both spectra show a prominent Amide I mode at ca. 1625 $cm^{-1}$ indicative of an amyloid-like material, similar to the parent barnacle glue.
Figure 5A:
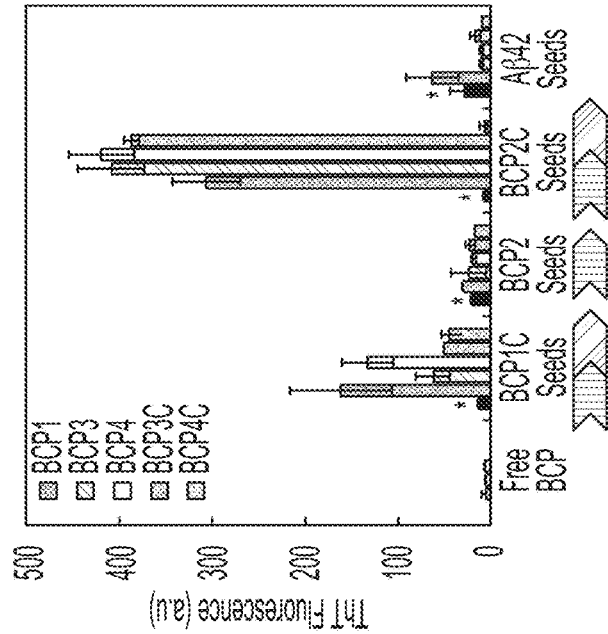
FIGS. 5A-5E show that the patterned charge domain in BCP2C confers molecular recognition by templating dormant BCPs to form fibrillar structures. Cross-seeding assay histograms are presented of preformed active BCP fibrils incubated with free BCPs in both Tris-EDTA (FIG. 5A) and ASW (FIG. 5B) are presented. Dormant BCP activation is defined as a ThT fluorescence≥100 a.u. The cross-seeding assay shows BCP2C to have the ability to activate most dormant peptides, which BCP2 and BCP1C do not showing the recognition of seeds is sequence specific. Seeds alone have a low intrinsic fluorescence indicated by *. Dormant peptide activation predominantly occurs with BCP2C exogenous seeds. Characteristic amyloid seeds of Aβ42 fibrils show no activation of BCPs.
Figure 5B:
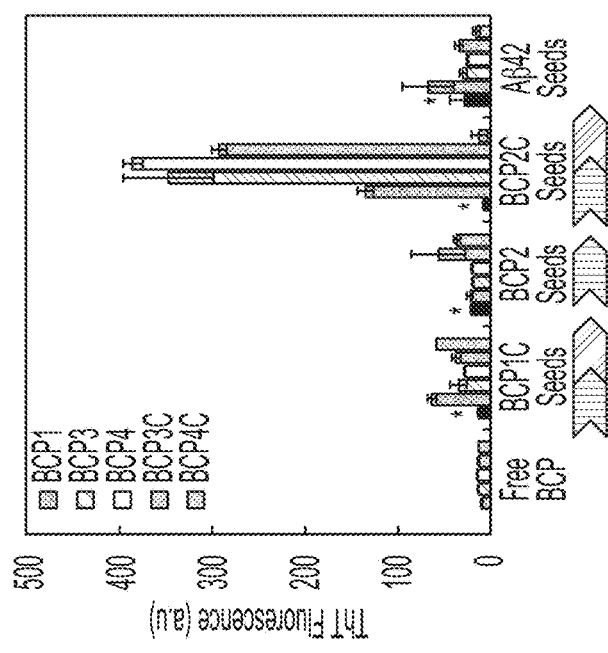
Figure 5C:
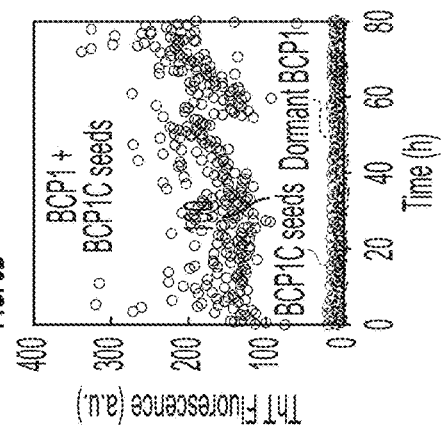
Figure 5D:
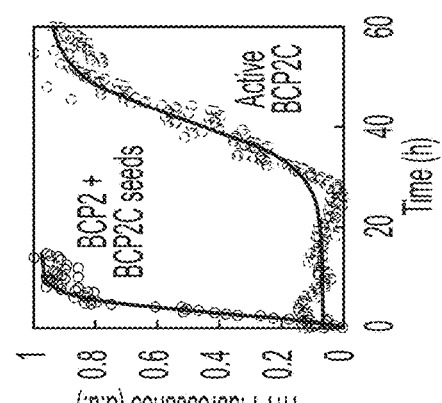
Figure 5E:
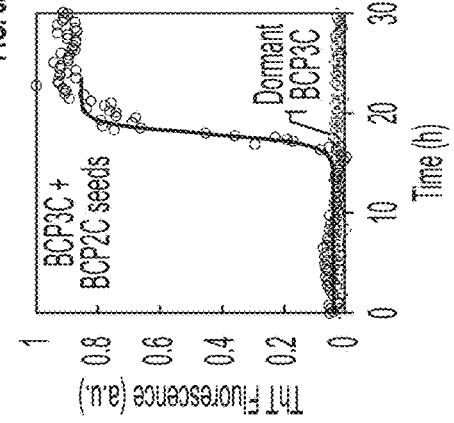

This assay technique may be used to monitor solution state kinetics exhibited by distinct solution phases (monomeric, oligomeric, protofibril and mature fiber) of well-studied amyloid proteins during fiber formation, as well as altered modes exhibited by the peptides of the invention (FIG. 4A-4B). This assay enables a rapid characterization of positive and negative responding candidates, which informs experimental design criteria such as pH, ionic strength, and peptide concentration that can overcome energy barriers for fiber nucleation. As an example, exposure of positively responding mimics to a charged mineral surface and subsequent imaging by atomic force microscopy (AFM) (FIG. 5A-5E) confirms an assembled glue-like fiber structure, and highlights their ability to form dense mat-like ultrastructures similar to bulk barnacle glue at the liquid-solid interface.

Assays of the invention include antibodies capable of binding to the peptide sequences of the invention. The antibodies preferably are provided along with one or more markers capable of binding to the antibody-peptide complex, and providing an indication that such binding has occurred. The indicator may be a visual indicator, a chemical indicator, a biological indicator, a radioactive indicator, or any other form of indicator known in the art.

The assays may be carried out using any suitable substrate. One presently-preferred substrate is a 96-well plate, but those skilled in the art will appreciate that the assays of the invention may be used in conjunction with other assay techniques and apparatus.

Methods.

The bioinspired nanofibers of the invention, which resemble the structure of amyloid materials, can bring multiple functions to a surface with a single deposition step. The invention establishes new methods of functionalizing surfaces, particularly wet surfaces or surfaces in an aqueous environment, where specific sequences polymerize to form gels and coatings that simultaneously add adhesive, mechanical, and advanced chemical or biological functionalities to diverse material surfaces.

The sequences and bioinspired nanofibers of the invention may be used for applications that include, but are not limited to, aqueous applications, undersea applications, and biomedical applications. New adhesives suitable for use in these and other aqueous environments are needed.

The peptides of the invention may be used in methods for forming an adhesive bond. One or more first peptides are applied to at least a portion of a first surface to be adhesively bonded to a second surface. The adhesive bond is then formed by placing a second peptide in contact with the first peptide. The second peptide may be placed in contact with the first peptide by any suitable technique. In some instances, this may occur by applying it to at least a portion of the second surface, and then contacting the first peptides on the first surface with the second peptides on the second surface. When the first peptide and the second peptide come into contact, the first and second peptides self-assemble into fibrils that result in adhesion between the first and second surfaces. In some aspects of the invention, the first peptide is selected from peptides having an amino acid sequence based on those set forth in any one of SEQ ID Nos:1-8 and 11-20. In further aspects of the invention, the second peptide is selected from peptides having an amino acid sequence based on those set forth in BCP2 and BCP2C (SEQ ID Nos:2, 6, 12, and 18).

Depending on the particular surfaces to be adhesively joined, the first surface may be provided in an aqueous environment, although the invention is not limited to the use of the adhesives in aqueous environments. When the first surface is in an aqueous environment, the aqueous environment may be a body of water, such as an ocean, sea, lake, or river, and the first surface may be a component of an underwater structure, such as a dock or offshore rig, or seagoing vessel, such as a ship or submarine.

The first surface may be also be a tissue of a plant or animal. Plant and animal tissues may be adhesively joined in order to repair wounds. In accordance with methods for adhesively joining tissue, the first peptides may be applied to a first tissue surface, and then joined with second peptides applied to a second tissue surface. When the peptides are brought together, the second peptides cause the formation of fibrils that result in adhesion between the first and second tissue surfaces.

In situ polymerization is also used to form injectable gels for tissue repair or as tissue adhesives and sutures in wet wound environments. Since BCP-based materials are held together by non-covalent bonds, hydrogels can be delivered as shear-thinned liquids that then re-assemble into gels at their injection site. This opens alternative technology avenues in developing injectable biomedical adhesive materials.

The peptides of the invention may be altered chemically by introducing new amino acids to the sequence or modifying existing amino acids to augment adhesive properties underwater. This can be done by replacing, for example, non-charged sequence positions with tyrosine residues and performing oxidation of the side chain to dihydroxyphenylalanine (DOPA). DOPA has been shown to displace water and form bidentate interactions with inorganic surfaces. Alternatively, serines in the existing sequence can be modified by chemical or biochemical means to display phosphate groups that mediate wet adhesion through divalent ions and ionic interactions with surfaces. Serines can also be modified with long or short chain polysaccharides, which promote adhesive interactions with inorganic surfaces. These modifications all enhance chemical adhesion of the formed material in underwater and/or saline environments.

EXAMPLES

The invention will now be particularly described by way of example. However, it will be apparent to one skilled in the art that the specific details are not required in order to practice the invention. The following descriptions of specific embodiments of the present invention are presented for purposes of illustration and description. They are not intended to be exhaustive of or to limit the invention to the precise forms disclosed. Many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated.

Example 1. Peptide Synthesis

Designer peptides were prepared on an automated solid-phase peptide synthesizer employing standard stepwise Fmoc protection and deprotection chemical procedures. Synthesis was carried out on a preloaded Fmoc-Val(tBu)-Wang low-loading support resin using HBTU activation chemistry, while 20% piperidine in DMF was employed to afford the Fmoc deprotection, monitored by UV absorbance at 301 nm. Peptides were cleaved off the support and side chain deprotected by stirring the resin-bound peptide in a cocktail containing 90:5:3:2 TFA/thioanisole/EDT/anisole under an $N_2$ atmosphere for ~6 h. Peptides were precipitated in cold ether and collected on vacuum filtration membrane, and lyophilized overnight. Purification of products was carried out by reverse-phase HPLC, where the most prominent peak was analyzed by MALDI-MS. Peptides and proteins were used as freeze-dried product and self-assembled at 1 mM concentrations at pH 8 in phosphate buffer to produce fibers.

Full length MRCP19 from *Megabalanus rosa* (acorn barnacle) was cloned and expressed recombinantly by GenScript USA.

Example 2. Peptide Preparation

Lyophilized, synthetic barnacle derived peptides were prepared according to published protocols of β-amyloid. In short, the peptides were treated with 200 μL hexafluoroisopropanol (HFIP) and sonicated (10 min) to dissolve preexisting or seed aggregates within the lyophilized stock. HFIP was evaporated off using a speedvac (Labconco), resulting in clear peptide films. These peptide films were dissolved in varying amounts of dimethyl sulfoxide (DMSO) to make a 10 mM stock solution of each BCP and sonicated (10 min). Stock solutions were stocked at −80° C. to prevent aggregation. To achieve the desired concentration, the stock solutions were dissolved directly into 50 mM Tris-HCl, 1 mM EDTA (Tris-EDTA) buffer, or sterilized Artificial Sea Water (ASW) with a salinity of 32 ppm. From the 10 mM stock solution of BCP1C/2/2C, 200 μM aggregated or seed solutions of these active (fibril forming) BCP peptides were prepared in their corresponding buffer (Tris or ASW) at 37° C. with orbital shaking for 48-96 hours, over 7-10 days.

Prepared fibrillar seeds were purified and concentrated in ~200 μL desired buffer for use in seeding assays. BCP2 and 2C formed large aggregates which were pelleted using a MiniSpin Plus (14.1 rcf, 30-60 min) (Eppendorf), decanted, and reconstituted in Tris-EDTA, ASW, or deionized water accordingly to 20 μM. For BCP2C, the presence of discrete fibrils inhibited pelleting and seeds were concentrated and used directly from stock concentrations. In addition, β-amyloid 1-42 (A1342) (Genscript USA, Inc., Piscataway, NJ) 10 mM stocks in DMSO were prepared using the same amyloid protocol above and seed solutions were formed over 300 hours and concentrated in Tris EDTA and ASW. Concentrated seed BCPs and seed A1342 were sonicated for 10-15 min immediately before use and ThT fluorescence of the seeds was checked prior to use in seeding assays. BCP2 underwent additional sonication (30% amplitude pulse for 5 min) with a sonic horn (Qsonica LLC, Newtown, CT) to ensure complete homogenization of BCP2 seeds. BCP1C/2/2C and mutBCP1 were used in seeding assays to activate non-fibril forming peptides in aggregation assays described below. A1342 seeds were used to see if non-active BCPs had specificity to amyloid-forming materials.

Example 3. Characterization of Peptide Polymerization

A stock solution of 1 mM ThT was prepared and a working solution of 100 μM ThT was used in each assay.

Two different ThT aggregation assays were performed: 1) Free peptide BCP and 2) Seeding from either BCP1C/2/2C or A1342 with free peptide BCP. In the free peptide BCP assay, each BCP (BCP1-4, BCP1C-4C, mutBCP1, and ranBCP2C) were prepared individually and ThT fluorescence measured at various concentrations (200 μM, 100 μM, and 50 μM) of each synthetic peptide. In addition to free peptide BCP, ThT assays were also performed with full length mrcp19 (1×) synthesized recombinantly (Genscript USA, Inc., Piscataway, NJ). In the seeded BCP assay, concentrated ~20 μM seed solutions of active (fibril forming) BCP1C/2/2C and A1342 were placed with dormant (non-fibril forming) BCP 1/3/3C/4/4C at 200 μM. Both ThT assays were incubated with 100 μM ThT at 32° C. in Grenier black bottom 96-microwell plates (Sigma-Aldrich) that were sealed to prevent evaporation. ThT fluorescence was measured every 15 min for up to 300 h using a Synergy H1 Hybrid Multi-mode reader (BioTek, Winooski, VT) with excitation and emission filters set at 440 and 480 nm, respectively with a low gain of 50, linear shaking, and top read. All ThT fluorescence assays were performed in duplicate (or more) on each plate and maximum fluorescence or normalized fluorescence was plotted in arbitrary units (a.u.). ThT assay results were verified among three or more independently performed experiments on additional 96 well plates. All kinetic data from ThT aggregation curves (free peptide BCP and seeded BCP assays) at each respective concentration were fit with a non-linear (sigmoidal) least squares regression to obtain estimated aggregation onset values/lag time ($T_{lag}$).[24]

$$F(t) = \frac{F_0 + A}{\left(1 + e^{-k\left(t - t_{\frac{1}{2}}\right)}\right)}$$

Fitted parameters of the least squares regressions are k (elongation rate constant), A (amplitude), $F_0$ (baseline), and $T_{1/2}$ (time at half completion of aggregation). As defined by Hellstrand, et al. $T_{lag}$ was calculated from the fitted parameters as:

$$T_{Lag} = T_{1/2} - \frac{2}{k}$$

Once modelled, the maximum fluorescence of the least squares fit for each sample was obtained. These maximum fluorescence measurements of two or more individual samples under identical experimental conditions (i.e. same concentration, seed preparation, temperature) were averaged and reported with standard deviation.

Example 4. Nanostructure Characterization by Atomic Force Microscopy

For ex situ AFM imaging, 20 μL samples from identified 96 microwells of interest were spotted onto freshly cleaved muscovite mica and placed in a hood to allow for evaporation of buffer to dryness (12-24 h). Each dry sample was washed with aliquots of deionized water and dried under a gentle stream of nitrogen. A Digital Instruments (Santa Barbara, CA) Dimension 3100 scanning probe microscope equipped with high frequency NanoSensors PPP-NCHR (NanoandMore USA, Lady's Island, SC) probes with a 42 N/m spring constant was used to image peptide nanostructures. All imaging was carried out under tapping mode, with 512×512 data acquisitions at a scan speed of 0.8 Hz at room temperature under acoustic isolation. Supplier-provided software (Nanoscope, V7.3, Veeco) was utilized for extracting quantitative data such as surface cross sections from AFM images. After images were collected, average feature widths were quantified by measuring the peak-to-peak distances over the span of multiple fibers.

Example 5. Observation of Fiber Formation

To establish experimental conditions that form fibers from designed mimics, a fluorometric assay was developed that is sensitive to ordered molecular structures, and has the ability to monitor growth kinetics for up to 96 simultaneous reactions spanning 48 hours while maintaining a constant volume in the hundred microliter range. This technique is used to monitor solution state kinetics exhibited by distinct solution phases (monomeric, oligomeric, protofibril, and mature fiber) of well-studied amyloid proteins during fiber formation, as well as altered modes exhibited by the designed peptide mimics. This assay enables a rapid characterization of positive and negative responding candidates, which informs experimental design criteria such as pH, ionic strength, and peptide concentration that can overcome energy barriers for fiber nucleation. As an example, exposure of positively responding mimics to a charged mineral surface and subsequent imaging by atomic force microscopy (AFM) (FIGS. 3A-3C) confirms an assembled glue-like fiber structure, and highlights their ability to form dense mat-like ultrastructures similar to bulk barnacle glue at the liquid-solid interface.

Figure 2A:
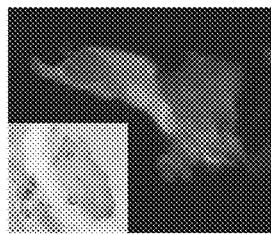
FIGS. 2A-2E show sequence-dependent polymerization of dormant and active BCPs.
Figure 2B:
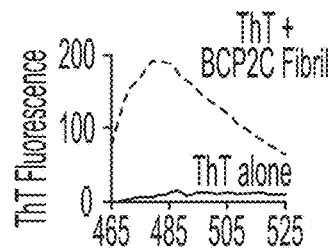
Figure 2C:
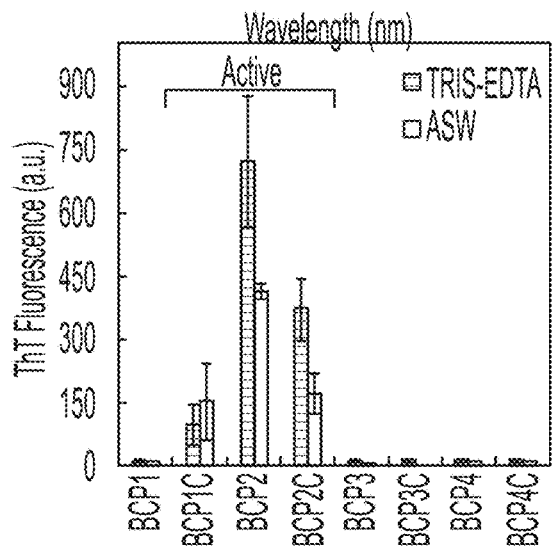
Figure 2D:
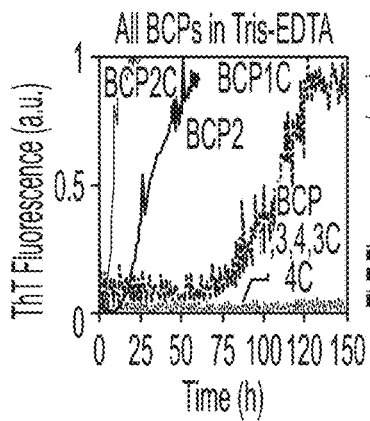
Figure 2D:
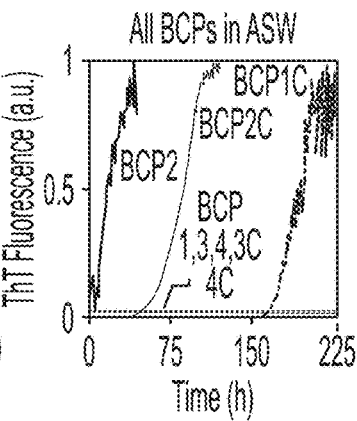
Figure 2E:
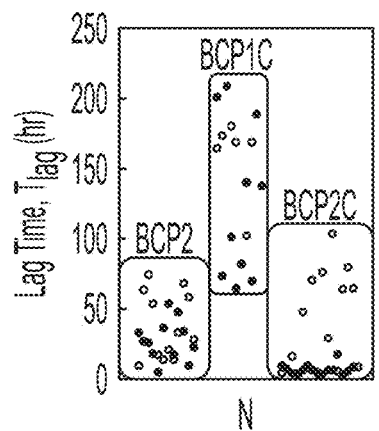
Figure 10:
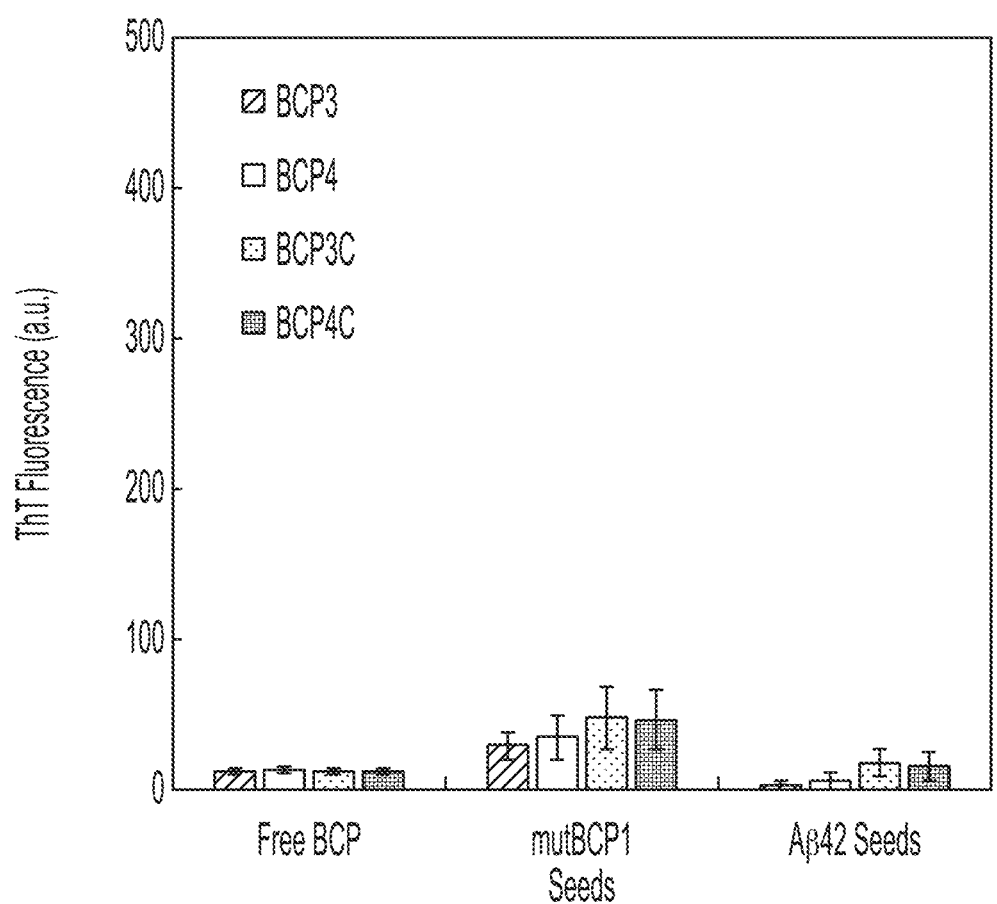
FIG. 10 Seed assay performed using mutBCP1 and Aβ42 seeds against BCPs 3/4/3C/4C showing little cross-seeding activity.

Of the surveyed sequences, only BCP2C is observed to polymerize and form nanofibers with the length and morphology of native glue fibers (compare FIG. 3C with FIGS. 3A and 3B). BCP1 and BCP2 also respond to ThT (FIGS. 3B and 3C), forming fibrils that display a short and bundled morphology. BCP1, BCP3, BCP3C, BCP4, and BCP4C display no activity and are referred to as dormant (FIG. 2C). BCP2C therefore is a likely candidate as a core sequence in forming native barnacle glue. To prove that this sequence is central in forming fibers, purified BCP2C fibers were exposed to BCPs that display dormant activity. In the presence of BCP2C seeds, shown in FIG. 10, higher ThT activity as well as more rapid polymerization of dormant BCPs over exposure to seeds prepared from BCP1 and BCP2 were observed. Therefore, the BCP2C sequence is found uniquely capable of activating other peptides to induce polymerization via molecular recognition.

Example 6. Barnacle Husbandry

*Amphibalanus amphitrite* barnacles were settled as cyprids on silicone-coated glass panels and reared at the Duke University Marine Laboratory (Beaufort, NC) as described previously (So, C. R. et al., "Oxidase Activity of the Barnacle Adhesive Interface Involves Peroxide-Dependent Catechol Oxidase and Lysyl Oxidase Enzymes," *ACS Appl Mater Interfaces* 9(13):11493-11505 (2017)). Panels of adult barnacles grown to 2-3 mm in diameter were shipped to the Naval Research Laboratory (Washington, DC), where they were maintained in an incubator operating at 23° C. on a 12 h day/night cycle in 32 ppt ASW (Instant Ocean, Blacksburg, VA). The barnacles were fed *Artemia* spp. *nauplii* (Brine Shrimp Direct, Ogden, UT) three times a week, and the ASW was changed once a week during which excess algal growth was removed. Barnacles used for experiments were gently dislodged from the silicone-coated panels, rinsed with distilled water, and placed on alternative substrates for the experiments.

Example 7. Immunoblotting of Barnacle Cement

Figure 7A:
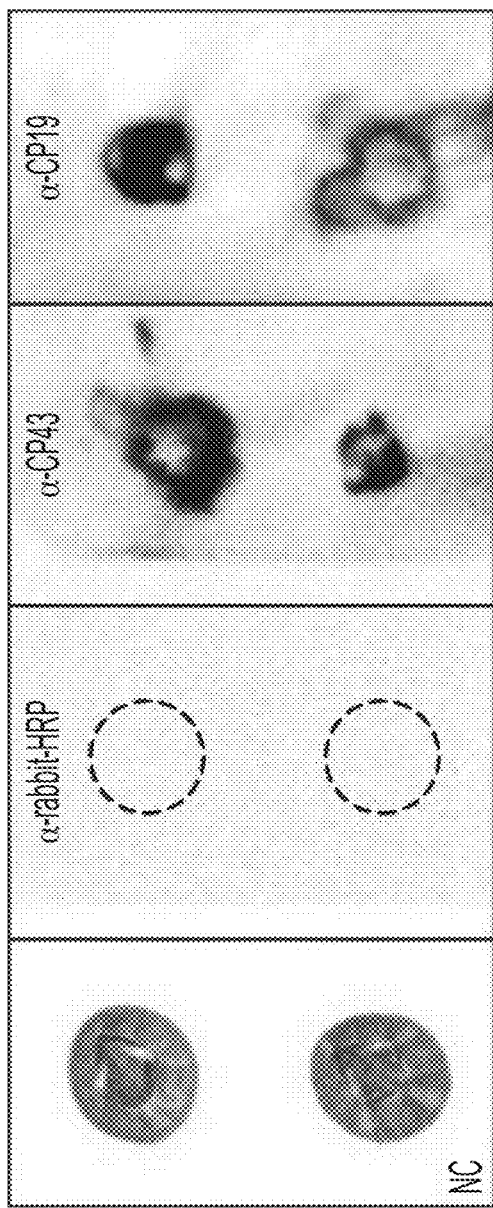

Adult barnacles were placed onto a nitrocellulose membrane (0.45 μm), fed and housed in ASW at room temperature for 72 hour settlement to allow for resettlement via cement deposition (FIG. 7A). After 72 hours, barnacles were gently peeled off (n=3) and the resultant membrane underwent Western immunoblotting. The membrane was blocked in 5% non-fat milk dissolved in 1×PBS-T, pH 7.4, (10 mM phosphate buffered saline, 0.05% Tween 20) for 1 hour, washed three times with PBS-T and probed with 1:1,000 dilution of anti-CP43 or anti-CP19 rabbit (FIG. 7B). The corresponding anti-rabbit HRP conjugated secondary antibody was used at 1:10,000 dilution (FIG. 7A). Membranes were developed using the Western Dura chemiluminescence kit (Pierce) and image acquisition via Gel Doc XR+ Gel Documentation System (Bio-Rad, Hercules, CA). Antibodies were generated by GenScript USA.

Example 8. Activity of Labeled BCP Towards Natural Glue Secretions

Figure 7C:
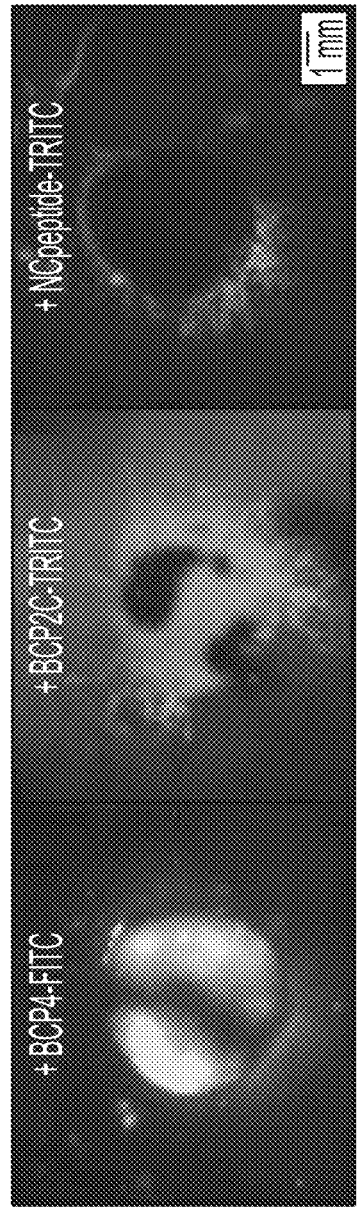

Adult barnacles were settled onto nitrocellulose membrane (0.45 pm) similar to immunoblotting experiments above. After 3 days, barnacles were peeled off (n=6) and the resultant membrane was blocked in 5% non-fat milk dissolved in 1×PBS-T, pH 7.4. Blocked membranes were washed three times in PBS-T and incubated overnight in 10 μM solutions of fluorescently labelled free BCPs, dormant BCP4-fluorescein-5-isothiocyanate (FITC) (max excitation 490 nm, max emission 525 nm) and active BCP2C-tetramethylrhodamine isothiocyanate (TRITC) (max excitation 557 nm, max emission 576 nm) (FIG. 7C). In addition, preformed BCP2C-TRITC seeds (100 μM) were formed at 37° C. with orbital shaking over 7-10 days. As negative controls, a solution of a TRITC-labeled peptide (GG-GRDGGG) was incubated with membrane deposited barnacle glue (FIG. 7C). Each incubation was repeated with multiple animals (n=3). Fluorescence microscopy images were collected on a Nikon A1R+ laser scanning confocal microscope to detect free and seeded BCPs over areas with transferred adhesive.

Example 9. Unique Core Sequences are Responsible for Polymerization of Materials To verify that amyloid-like barnacle adhesive responds to Thioflavin T (ThT), exposed untreated glue shavings (a.k.a., gummy glue) were taken directly from the barnacle *Amphibalanus amphitrite* to ThT. ThT is a cationic benzothiazole dye that probes for beta sheet rich structures responsible for holding amyloid fibrils together. Shown in FIG. 2A, natural glue shavings demonstrate enhanced ThT fluorescence response after a 15-30 minute incubation at room temperature, verifying that the natural adhesive responds to dyes sensitive to classical amyloids in agreement with previous studies highlighting the amyloid-like structure using FTIR and CD.

The formation of amyloids is commonly classified as a nucleation-dependent polymerization reaction with a characteristic initial lag phase, followed by an elongation/growth phase during which most fibrils form, and ending in a plateau of no further amyloid fibril increase. The physical states of aggregation can be classified based on a classical sigmoidal curve produced as ThT-responsive materials form over time in solution, including stages of fibril growth that spans monomers, oligomers, protofibrils, and mature fibrils. To determine physical properties of representative patterned BCPs, all eight peptides were surveyed by exposing them to ThT solution over the course of up to 300 hours. Of the BCPs, three distinct peptide sequences (BCP1C/2/2C) demonstrate the characteristic sigmoidal curvature associated with fibril formation (FIG. 2D) and a positive ThT response (maximum fluorescence) (FIG. 2C) in both simple buffer and seawater conditions. In contrast, BCPs 1/3/3C/4/4C displayed no activity or fibril formation over 300 h, and are referred to as dormant BCP sequences (FIG. 2C). In both Tris-EDTA and artificial seawater (ASW), BCP2 shows the highest activity, followed by BCP2C and BCP1C which both contain charged domains. All three active peptides responded and underwent fibril formation in an artificial sea water environment with similar onset times as in Tris-EDTA, largely unaffected by free ions present in ASW. The lag time ($T_{lag}$) is the time at which aggregation begins, defined as an x-intercept extrapolated from the rising linear portion of the sigmoid. Seen in FIG. 2E, $T_{lag}$ values were obtained using a sigmoidal model fitted by least squares regression of each experimental curve. ThT fluorescence curves (FIG. 2D) and estimated aggregation onset times (FIG. 2E) reveal that BCP2/2C exhibit faster aggregation onset times with $T_{lag}$ values within ca. 12 h in Tris-EDTA and ca. 50 h in ASW. In contrast to BCP1, BCP1C is considerably slower with a delayed aggregation time of 100+ hours. In Tris-EDTA, BCP2C noticeably had the shortest aggregation time with the lowest spread of $T_{lag}$ (2-16 h, median 6 h), followed by BCP2 (4-53 h, median 26 h), while BCP1C exhibited the longest aggregation time (64-208 h, median 120 h). BCP2C/2 revealed a large $T_{lag}$ spread ranging from 2-102 h (median 22 h) and 9-73 h (median 30 h) respectively. BCP1C remained the slowest with an onset of 101-180 h (median 169 h). The aggregation onset of fibrillar formations follows the trend BCP2C<BCP2<BCP1C for both Tris-EDTA and ASW with BCP1C being significantly delayed.

Figure 3:
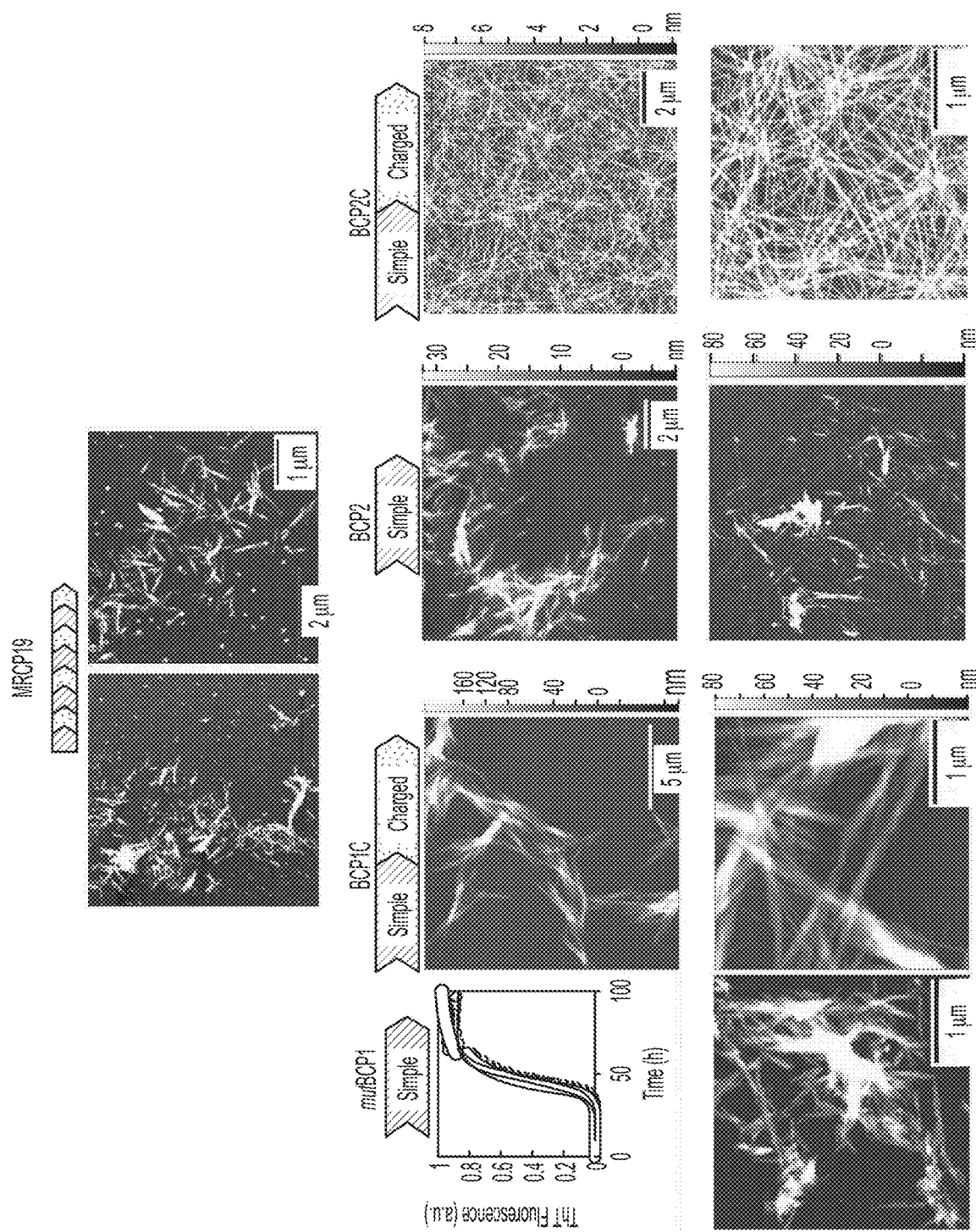
FIG. 3 shows the nano and microstructure of formed BCP fibrils from ThT screening. The top image corresponds to the full-length protein MRCP19 forming short fibers that clump together. The image on the left shows the point mutated mutBCP1 (G19C) peptide demonstrating classical nucleation, lag phase and growth, also forming short fibrils that aggregate, adjacent to (right) BCP1C, containing an additional neighboring charged domain to result in fibers that are 5+ microns in length. The next image to the right shows BCP2, with only a simple domain, forming a similar fiber structure as shown for MRCP19, where short assemblies clump to form larger particles. The image furthest right shows BCP2C fibrils, including an additional neighboring patterned charge domain that forms 5+ micron long fibrils with a discrete meshed architecture.

Example 10. Charged Patterns Confer Folded, Microns-Long Fibril Morphology to Simple Sequences To understand the effect of charged domains on the morphology and molecular structure of peptide fibrils, ThT responsive materials were characterized by AFM and FTIR (FIGS. 3 and 4A-4B, respectively). Clear morphological and structural differences were observed between simple peptides alone (BCP1/2) and peptides that also contained a variable charged sequence (BCP1C/2C). This is highlighted in FIG. 3, where simple peptides assemble into short branched structures spanning 1-2 microns, similar to the full length protein, while their charged counterparts assemble into features that span 5+ microns. The difference between BCP2 and BCP2C is especially stark, where the charged sequence confers a matted discrete structure while the simple peptide alone clumps as aggregates from shorter subunit fibrils. Whole length 19 kD protein from *Megabalanus rosa* (MRCP19), containing all homologous domains, forms very short fibers that do not exceed 1 micron which is consistent with other observations. Since BCP1 showed no ability to assemble on its own, a single gly→cys mutation (G19C, mutBCP1) was introduced to promote intermolecular interactions through disulfide bonds. Indeed, like the other active peptides, a single mutation in mutBCP1 induced classical aggregation, lag and fiber growth phases when the solution was monitored using ThT. Fibers formed by mutBCP1 are similar to those of another simple peptide, BCP2, in that fibers remain in the 1-2 micron range, yet are 5+ microns in the presence of the neighboring charged domain as seen in BCP1C and 2C.

Example 11. Transmission Infrared Spectroscopy of Peptide Nanofibers Dried on CaF2 Reveal Clear Distinctions in the Secondary Structure of Sequences that Contain Patterned Charge Domains Shown in FIGS. 4A-4B, all fibril materials formed by peptides absorb strongly in the Amide I region, with the largest peak centered at ca. 1623 $cm^{-1}$ typical of tightly folded beta-strand secondary structures. Two other prominent features range from 1655-1660 $cm^{-1}$ for all peptide fibrils as well as a prominent shoulder at 1698 $cm^{-1}$ for BCP1C/2C. The broad Amide I feature at ca. 1660 $cm^{-1}$ is also present in amyloid beta. However, the unique mode at 1698 $cm^{-1}$ observed in conjunction with the narrow mode observed at ca. 1625 $cm^{-1}$ indicates that peptides BCP1C and BCP2C form beta strands oriented in an anti-parallel fashion. In contrast, fibrils made from peptides without charged domains (mutBCP1 and BCP2) do not display the 1698 $cm^{-1}$ mode, consistent with a parallel beta sheet structure. Quantification of the maximum peak absorbance at 1698 $cm^{-1}$ as a fraction of the peak at ca. 1625 $cm^{-1}$ highlights large differences in the two vibrational modes between charged and non-charged peptides. Peptides with charged domains BCP2C and BCP1C have fractions in the 0.9-1.0 range (when normalized to 1), while the absence of the feature at 1698 $cm^{-1}$ causes BCP2 and mutBCP1 to exhibit low fractions between 0.15 and 0.3 (FIG. 9). These data suggest that patterned charge domains confer an anti-parallel structure to formed fibrils.

Example 12. Patterned Charge Domains Activate Dormant Barnacle Cement Peptides Through Molecular Recognition Since charged and non-charged domains appear in a sequential order along the natural protein sequences (FIG. 1), the ability of organized seed structures to serve as templates in activating peptides from downstream regions was tested. To this end, the ability of BCP fibrils (BCP1C/2/2C) to polymerize dormant BCPs (BCP1/3/3C/4/4C) or accelerate kinetics of fibril formation was probed using a cross-seeding ThT reaction in both Tris-EDTA (FIG. 5A) and ASW (FIG. 5B). For this, BCP seeds were formed over 7-10 days in Tris-EDTA, purified and incubated with free peptide solutions. Fibrillar BCP seeds alone have a low inherent ThT fluorescence over 300 h. Activation of dormant peptides was measured and counted only if the fluorescence exceeded the minimum response of active BCPs, i.e., ≥100 a.u. Interestingly, while BCP2 and mutBCP1 form fibrils as free peptides, they lack an ability to stimulate elongation and activation of dormant BCPs (FIG. 10). Seeds from peptides without charged domains have little activity, while seeds containing charged domains initiate the polymerization of most dormant peptides in both Tris-EDTA and ASW. The charged domain present in both BCP1C and BCP2C, as well as their unique anti-parallel secondary structure, adds a component of recognition for dormant peptide sequences not observed in mutBCP1 or BCP2. This robust recognition establishes BCP2C as the most self-active, as well as activity inducing, sequence of the eight peptides studied. This is exemplified in FIG. 5C, where dormant peptide BCP3C is placed in a cross-seeding assay with preformed fibrils of BCP2C. While no measured onset over 300 h is observed (FIGS. 2C and 2D) for dormant BCP3C alone, the peptide polymerizes in the presence of BCP2C seeds in under 17 h. Furthermore, seeding by BCP2C not only activates most dormant peptides, but also accelerates the formation of amyloid fibrils in active peptides such as BCP2. The lag phase for cross-seeded reactions of active free BCP2 was <2 h in the presence of BCP2C seeds, compared to 25-30 h for unseeded reactions (FIG. 5D).

Interestingly, BCP1C is observed to only activate peptides BCP1 and 4 in ASW (FIG. 5B). Similar to BCP2C, BCP1C contains both a simple and charged domain and is shown to template polymerization of its simple domain (BCP1) counterpart. While BCP1 alone has no measured onset over 300 h, it readily polymerizes at 30 h in the presence of BCP1C seeds (FIGS. 2C and 2D). Thus, peptides displaying a patterned charge domain are uniquely capable of inducing downstream dormant peptides to form amyloid fibers, possibly due to the anti-parallel configuration of fibers. BCPs were then exposed to a well-known amyloid seed organized in a parallel beta sheet structure, human beta-amyloid 1-42 (AB42), to determine whether this response is specific to barnacle adhesives. In these assays, no ThT response (FIGS. 5A and 5B) was observed with AB42 fibrils, showing that polymerization is specific to barnacle glue materials and the unique secondary structures formed by alternating charged/non-charged sequences.

Example 13. Randomization of BCP2C Sequence Eliminates Propensity for Polymerization and Recognition To test the importance of the linear sequence in both the polymerization and activation of downstream sequences, the BCP2C sequence was randomized, and ThT activity and aggregation activity was monitored (FIGS. 6A and 6B). Upon randomization, the N-terminal hydrophobic core sequence and corresponding amphiphilic nature were disrupted, shifting the C-terminus of the peptide to become more hydrophobic (FIG. 6B). Interestingly, ranBCP2C showed no ThT activity over 300 h (FIG. 6C), showing that it could no longer polymerize into fibrillar structures like that of its predecessor BCP2C, and that a sequence without amphiphilic property or an alternating charge pattern can no longer undergo recognition and assembly.

Example 14. BCPs Bind to Naturally Secreted Barnacle Adhesive

The ability for short BCP sequences to recognize naturally secreted adhesive from *A. Amphitrite* acorn barnacles was tested. Antibodies generated against adhesive proteins as well as two fluorescently labeled BCPs were used as probes against nitrocellulose membranes where barnacles have been resettled for three days. The presence of AA19 and AA43, two proteins in the adhesive abundant in non-charged amino acids, were first probed to verify that they had been transferred to the membrane surface. FIG. 7 shows a strong response to the primary antibodies, with little or no background response compared to the secondary antibody alone. Negative controls with luminol, a peroxidase activated chemiluminescent substrate, showed little cross reactivity with endogenous peroxidases known to exist in the barnacle adhesive. Both antibodies reacted strongly to regions where the organism resided, where proteins are seen distributed either localized to the barnacle periphery where new growth occurs or filled into the center of the settled region. A second set of membranes were probed with BCP2C and BCP4 peptides labelled with TRITC and FITC, respectively. A negative control peptide containing a GGGKDGGG sequence sensitive to oxidases was used, which showed no activity towards the glue region. Both BCP4 as well as BCP2C displayed strong fluorescence when exposed to the transferred glue region, demonstrating that there is an element of recognition for BCPs by the natural glue materials.

DISCUSSION

Figure 11:
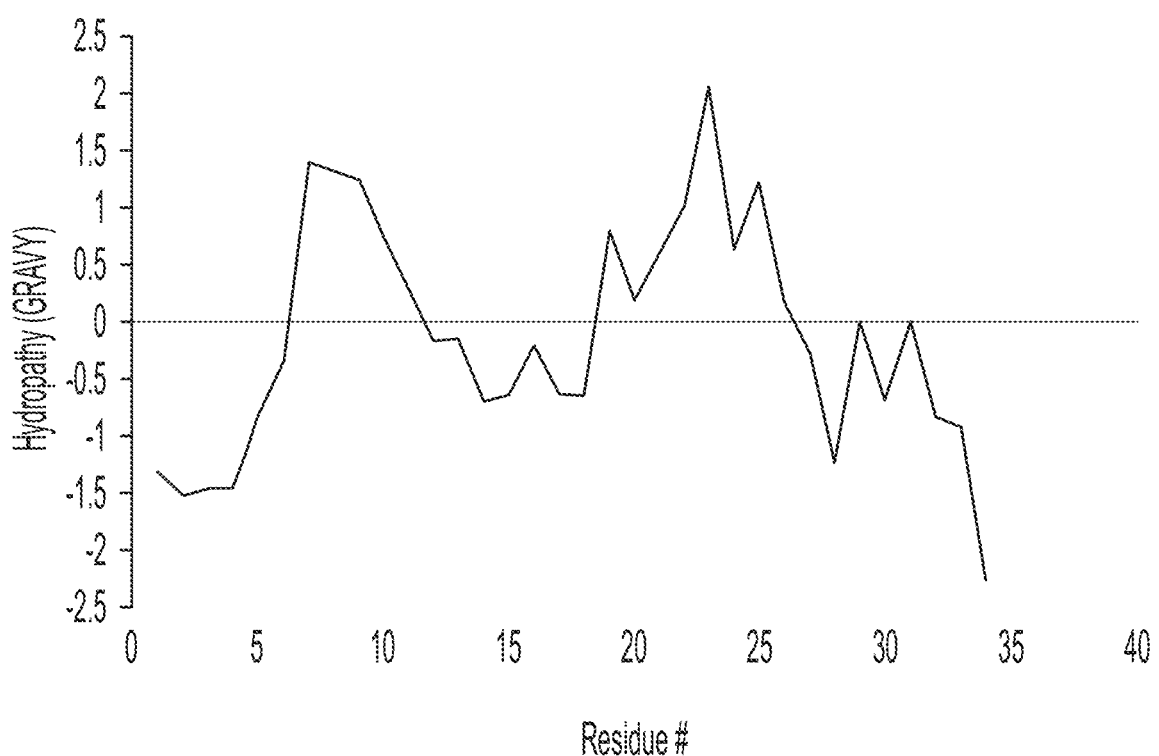
FIG. 11 is a Kyte and Doolittle hydropathy plot of BCP1C showing hydrophobic stretch across residues 7-11.

The unique primary sequence of BCP2C enables it to serve as a core aggregation domain, form extended fibril structures similar to barnacle glue, and activate most other dormant peptide sequences in both Tris-EDTA and ASW. Since fibril formation is largely unaffected by solution ionic strength, hydropathy trends in the BCP2C sequence were examined (FIG. 6A). Much like in amyloid beta and designed beta sheet structures, hydrophobic sequences may play a central role in folding, activation, and self-assembly of BCP2C fibrils. The 37 residue sequence of BCP2C contains both a simple, non-charged domain (BCP2) where three aliphatic residues V7, V12, and 114 form an 11-residue hydrophobic segment (average hydropathy >3) that abruptly transitions to a charged and hydrophilic C-terminal region. Aggregative hydrophobic domains such as those found in BCP2 may also be 'gated' by alternating charged residues, which can explain the lack of polymerization in BCP1 and long delayed onset of nanofiber formation in BCP1C. BCP1 contains only one central aliphatic valine, while BCP1C contains two leucines and an isoleucine alternating with two aspartic acids in a 5-residue stretch (FIG. 11). These three aliphatic residues may be prevented from interacting due to negative charge repulsion from neighboring aspartic acid side chains, adding substantial time to achieve necessary aggregation.

Figure 8:
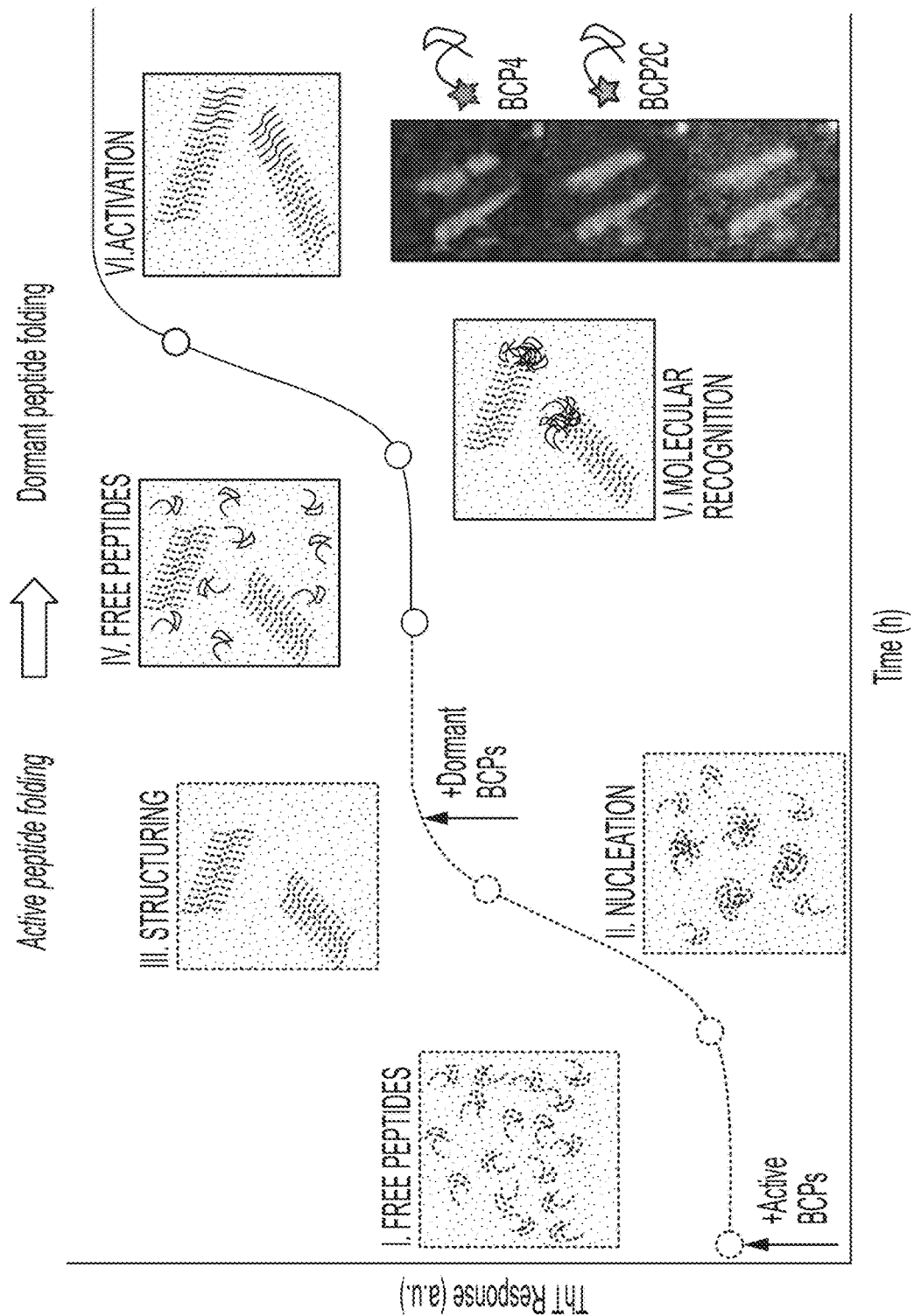
FIG. 8 shows the mechanism of dormant peptide activation through molecular recognition. Two classical sigmoidal curves are involved in the recognition process, indicating that the full physical aggregation and growth mechanism occurs first from the self-assembling peptide (I-III) and secondly from the dormant peptide recognizing the nascent structured active peptide template (IV-VI). Inset fluorescence microscopy of TRITC labelled BCP2C seeds exposed to FITC labelled BCP4 free peptide show coincident red and green fluorescence, indicative of a layer-by-layer growth of BCP4 onto pre-existing BCP2C seeds.
Figure 9:
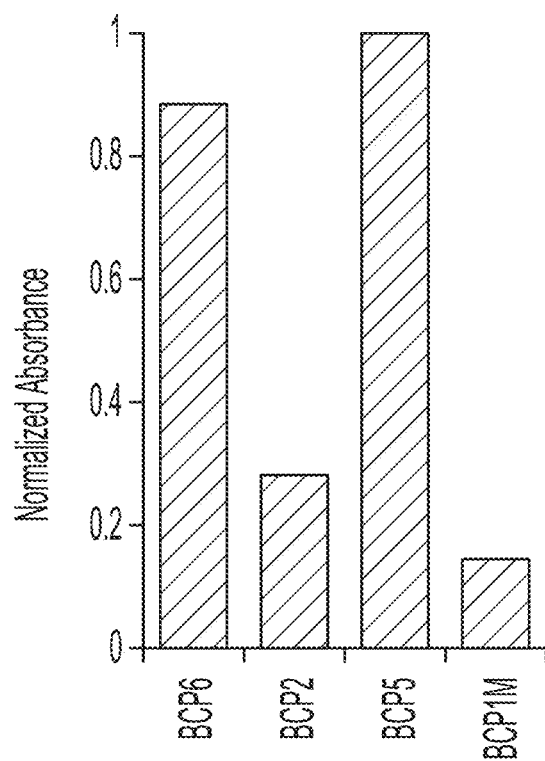
FIG. 9 shows raw and normalized absorbance data from FTIR as a ratio of 1625 cm$^{-1}$ to 1698 cm$^{-1}$.

These examples demonstrate that BCPs derived from patterned barnacle cement proteins undergo a process of induced fit occurring through reversible interactions, principally structured hydrogen bonding, to form complex nanomaterials as they first exist as free peptides and only become active in material formation when induced by a unique anti-parallel folded template. Two classical sigmoidal curves were observed during the activation process: one for the active sequence and a subsequent curve for the nucleation and growth of dormant peptides. The observation of a second complete curve indicates that dormant peptides undergo the full physical process of fiber assembly in the presence of structured templates. This mechanism is outlined in FIG. 8, where the activation of a dormant peptide follows a typical protein-protein recognition scheme: I) Free peptides exist in solution displaying little structure, II) peptides coalesce and assemble into nucleates, III) nucleates condense into structured beta-sheet fibrils, IV) structured peptides from III are now recognized by free dormant peptides, V) dormant peptides undergo nucleation and typical sigmoidal growth from existing seeds, and finally VI) nucleates collapse into beta-sheet structures to form multi-component fibrils. As protein folding begins with nearest neighbor interactions, two pathways would lead to BCP2C existing in an active folded structure: first, BCP2 being hydrophobic would induce the neighboring patterned charge domain to fold into an anti-parallel configuration within the same protein. This starting structure then templates the folding of subsequent sequences into a fiber comprised of 19-like proteins. Secondly, since peptides are observed to complement with the natural adhesive, homologous BCP2 domains from two proteins could condense through hydrophobic interactions to allow neighboring charged domains in BCP2C to fold and initiate the activation process of downstream domains in the same protein or among multiple proteins.

Although BCPs are abundant in charged residues, a consistent finding is that polymerization occurs similarly in both artificial seawater and simple buffers or DI $H_2O$, solutions of diverse ionic strength. This implies that charged residues play a minor role in forming fibers, emphasizing a mechanism where fibrils are formed through flexible non-charged side-chains and hydrogen bonds, similar to other fibrous biomaterials. Assembly and formation of underwater materials through simple hydrophobic aggregation would allow the organism to operate in seawater and form materials in the presence of metal ions. Opposite to highly aggregative domains, the ability for certain domains to completely resist polymerization indicates that there also exist so-called "gatekeeping" domains which act as a delay for proteins to form materials. Although BCP2C and BCP2 polymerize rapidly, certain domains took over 100 hours, or 3-4 days, to become active even in the presence of a BCP2C template. This indicates that even in partially folded and activated states, there exist segments which delay the curing process of glue components on the timescale of real barnacle molting and growth processes.

Fibrillar amyloid structures used by barnacles are unique among marine foulants, yet they bear similar alternating sequences to specialized protein fibrils used by arthropods and crustaceans. These include nanofibrous adhesive protein produced by distantly related spiders, pyriform spidroin. These materials resemble barnacle glue, as they exist as an embedded nanofibrous meshwork that envelops a central dragline. Pyriform spidroin proteins do not exhibit the conventional subrepeat motifs found in spider fibroin, rather they display regions of alternating polar and nonpolar amino acids, similar to the barnacle adhesive. Two examples include the primary repeated region as well as the more variable region from the primary pyriform spidroin protein PySp1. The non-charged residues in the latter motif are polymorphic, similar to the observed pattern in barnacle adhesive proteins. Further, S-X and G-X motifs in silk fibroin proteins directly relate to the ability to produce turns in shaping the threads produced by silk worms.

The alternating sequences present in barnacle adhesive induce folding when in tandem with conserved segments that exist in at least 10 locations across multiple proteins. Spiders, moths and silk-producing crustaceans are closer relatives to barnacles than the well-studied adhesives of bivalves such as mussels and tube worms, which bear no significant chemical or structural similarity to barnacle adhesive.

CONCLUSIONS

Alternating binary patterns of charge throughout homologous cement proteins from the barnacle adhesive were found to confer a unique folded secondary structure that enables polymerization of downstream dormant cement sequences. These dormant peptides only polymerize in the presence of an anti-parallel structure, highlighting molecular recognition as a key mechanism in the formation of amyloid-like adhesives produced by the barnacle. The invention demonstrates that the structures produced by patterned cement sequences, and the progression of domain interactions, are critical in polymerizing materials that resemble the natural adhesive. The sequences of the invention define a basic syntax used by the barnacle to fabricate its adhesive, but also add new functions to the growing language of materials formation through simple non-charged amino acid sequences.

It will, of course, be appreciated that the above description has been given by way of example only and that modifications in detail may be made within the scope of the present invention.

Throughout this application, various patents and publications have been cited. The disclosures of these patents and publications in their entireties are hereby incorporated by reference into this application, in order to more fully describe the state of the art to which this invention pertains.

The invention is capable of modification, alteration, and equivalents in form and function, as will occur to those ordinarily skilled in the pertinent arts having the benefit of this disclosure. While the present invention has been described with respect to what are presently considered the preferred embodiments, the invention is not so limited. To the contrary, the invention is intended to cover various modifications and equivalent arrangements included within the spirit and scope of the description provided above.

What is claimed:

1. A peptide comprising the amino acid sequence as set forth in any one of SEQ ID Nos:1-8.

2. The peptide of claim 1, wherein the peptide has the amino acid sequence selected from the group consisting of SEQ ID No:2, SEQ ID No:5, and SEQ ID No:6.

3. The peptide of claim 2, wherein the peptide aggregates to form fibrils.

4. The peptide of claim 1, wherein the peptide has the amino acid sequence selected from the group consisting of SEQ ID No:1, SEQ ID No:3, SEQ ID No:4, SEQ ID No:7, and SEQ ID No:8.

5. The peptide of claim 4, wherein peptide does not aggregate.

* * * * *

```
                             SEQUENCE LISTING

Sequence total quantity: 36
SEQ ID NO: 1           moltype = AA  length = 22
FEATURE                Location/Qualifiers
REGION                 1..22
                       note = synthetic construct
source                 1..22
                       mol_type = protein
                       organism = synthetic construct
SEQUENCE: 1
QTGYTRGGAA VSSTGATQGA GS                                                  22

SEQ ID NO: 2           moltype = AA  length = 25
FEATURE                Location/Qualifiers
REGION                 1..25
                       note = synthetic construct
source                 1..25
                       mol_type = protein
                       organism = synthetic construct
SEQUENCE: 2
AVGNSGVSGS GVSIGDSGFR QKTQT                                               25

SEQ ID NO: 3           moltype = AA  length = 24
FEATURE                Location/Qualifiers
REGION                 1..24
                       note = synthetic construct
source                 1..24
                       mol_type = protein
                       organism = synthetic construct
SEQUENCE: 3
TGTQGKGITS GEAVANQKAG AEGG                                                24

SEQ ID NO: 4           moltype = AA  length = 21
FEATURE                Location/Qualifiers
REGION                 1..21
                       note = synthetic construct
source                 1..21
                       mol_type = protein
                       organism = synthetic construct
SEQUENCE: 4
GTSSSGHKAS SSGPGRFITS N                                                   21

SEQ ID NO: 5           moltype = AA  length = 38
FEATURE                Location/Qualifiers
REGION                 1..38
                       note = synthetic construct
source                 1..38
                       mol_type = protein
                       organism = synthetic construct
SEQUENCE: 5
QTGYTRGGAA VSSTGATQGA GSLDLAIDGP GGFKARSK                                 38

SEQ ID NO: 6           moltype = AA  length = 37
FEATURE                Location/Qualifiers
REGION                 1..37
                       note = synthetic construct
source                 1..37
                       mol_type = protein
                       organism = synthetic construct
SEQUENCE: 6
AVGNSGVSGS GVSIGDSGFR QKTQTNSEAG SKGTKRA                                  37
```

```
SEQ ID NO: 7            moltype = AA   length = 48
FEATURE                 Location/Qualifiers
REGION                  1..48
                        note = synthetic construct
source                  1..48
                        mol_type = protein
                        organism = synthetic construct
SEQUENCE: 7
TGTQGKGITS GEAVANQKAG AEGGAQRVEA VKYVESDGKN LYKVEKVD                 48

SEQ ID NO: 8            moltype = AA   length = 35
FEATURE                 Location/Qualifiers
REGION                  1..35
                        note = synthetic construct
source                  1..35
                        mol_type = protein
                        organism = synthetic construct
SEQUENCE: 8
GTSSSGHKAS SSGPGRFITS NEVGTEIKLT TPELD                               35

SEQ ID NO: 9            moltype = AA   length = 22
FEATURE                 Location/Qualifiers
REGION                  1..22
                        note = synthetic construct
source                  1..22
                        mol_type = protein
                        organism = synthetic construct
SEQUENCE: 9
QTGYTRGGAA VSSTGATQCA GS                                            22

SEQ ID NO: 10           moltype = AA   length = 37
FEATURE                 Location/Qualifiers
REGION                  1..37
                        note = synthetic construct
source                  1..37
                        mol_type = protein
                        organism = synthetic construct
SEQUENCE: 10
GKRSGQDGTT TSGNVSETSS SFVKGKAAVG RGQINSA                             37

SEQ ID NO: 11           moltype = AA   length = 22
FEATURE                 Location/Qualifiers
REGION                  1..22
                        note = synthetic construct
SITE                    2
                        note = misc_feature - Xaa is a naturally occurring amino
                         acid selected from Gly, Ser,Thr, Ala, Val, Ile, Lys, Arg,
                         Glu, Asp, Asn, Gln
SITE                    4
                        note = misc_feature - Xaa is a naturally occurring amino
                         acid selected from Gly, Ser,Thr, Ala, Val, Ile, Lys, Arg,
                         Glu, Asp, Asn, Gln
SITE                    6
                        note = misc_feature - Xaa is a naturally occurring amino
                         acid selected from Gly, Ser,Thr, Ala, Val, Ile, Lys, Arg,
                         Glu, Asp, Asn, Gln
SITE                    10
                        note = misc_feature - Xaa is a naturally occurring amino
                         acid selected from Gly, Ser,Thr, Ala, Val, Ile, Lys, Arg,
                         Glu, Asp, Asn, Gln
REGION                  13..14
                        note = misc_feature - Xaa is a naturally occurring amino
                         acid selected from Gly, Ser,Thr, Ala, Val, Ile, Lys, Arg,
                         Glu, Asp, Asn, Gln
SITE                    16
                        note = misc_feature - Xaa is a naturally occurring amino
                         acid selected from Gly, Ser,Thr, Ala, Val, Ile, Lys, Arg,
                         Glu, Asp, Asn, Glnd
SITE                    20
                        note = misc_feature - Xaa is a naturally occurring amino
                         acid selected from Gly, Ser,Thr, Ala, Val, Ile, Lys, Arg,
                         Glu, Asp, Asn, Gln
source                  1..22
                        mol_type = protein
                        organism = synthetic construct
SEQUENCE: 11
QXGXTXGGAX VSXXGXTQGX GS                                            22
```

| | | |
|---|---|---|
| SEQ ID NO: 12 | moltype = AA  length = 21 | |
| FEATURE | Location/Qualifiers | |
| REGION | 1..21 | |
| | note = synthetic construct | |
| SITE | 10 | |
| | note = misc_feature - Xaa is a naturally occurring amino acid selected from Gly, Ser,Thr, Ala, Val, Ile, Lys, Arg, Glu, Asp, Asn, Gln | |
| SITE | 12 | |
| | note = misc_feature - Xaa is a naturally occurring amino acid selected from Gly, Ser,Thr, Ala, Val, Ile, Lys, Arg, Glu, Asp, Asn, Gln | |
| SITE | 14 | |
| | note = misc_feature - Xaa is a naturally occurring amino acid selected from Gly, Ser,Thr, Ala, Val, Ile, Lys, Arg, Glu, Asp, Asn, Gln | |
| SITE | 16 | |
| | note = misc_feature - Xaa is a naturally occurring amino acid selected from Gly, Ser,Thr, Ala, Val, Ile, Lys, Arg, Glu, Asp, Asn, Gln | |
| SITE | 18 | |
| | note = misc_feature - Xaa is a naturally occurring amino acid selected from Gly, Ser,Thr, Ala, Val, Ile, Lys, Arg, Glu, Asp, Asn, Gln | |
| SITE | 20 | |
| | note = misc_feature - Xaa is a naturally occurring amino acid selected from Gly, Ser,Thr, Ala, Val, Ile, Lys, Arg, Glu, Asp, Asn, Gln | |
| source | 1..21 | |
| | mol_type = protein | |
| | organism = synthetic construct | |
| SEQUENCE: 12 | | |
| AVGNSGVSGX GXSXGXGXFX Q | | 21 |
| | | |
| SEQ ID NO: 13 | moltype = AA  length = 26 | |
| FEATURE | Location/Qualifiers | |
| REGION | 1..26 | |
| | note = synthetic construct | |
| SITE | 2 | |
| | note = misc_feature - Xaa is a naturally occurring amino acid selected from Gly, Ser,Thr, Ala, Val, Ile, Lys, Arg, Glu, Asp, Asn, Gln | |
| SITE | 4 | |
| | note = misc_feature - Xaa is a naturally occurring amino acid selected from Gly, Ser,Thr, Ala, Val, Ile, Lys, Arg, Glu, Asp, Asn, Gln | |
| SITE | 6 | |
| | note = misc_feature - Xaa is a naturally occurring amino acid selected from Gly, Ser,Thr, Ala, Val, Ile, Lys, Arg, Glu, Asp, Asn, Gln | |
| SITE | 8 | |
| | note = misc_feature - Xaa is a naturally occurring amino acid selected from Gly, Ser,Thr, Ala, Val, Ile, Lys, Arg, Glu, Asp, Asn, Gln | |
| SITE | 10 | |
| | note = misc_feature - Xaa is a naturally occurring amino acid selected from Gly, Ser,Thr, Ala, Val, Ile, Lys, Arg, Glu, Asp, Asn, Gln | |
| SITE | 12 | |
| | note = misc_feature - Xaa is a naturally occurring amino acid selected from Gly, Ser,Thr, Ala, Val, Ile, Lys, Arg, Glu, Asp, Asn, Gln | |
| SITE | 14 | |
| | note = misc_feature - Xaa is a naturally occurring amino acid selected from Gly, Ser,Thr, Ala, Val, Ile, Lys, Arg, Glu, Asp, Asn, Gln | |
| REGION | 16..18 | |
| | note = misc_feature - Xaa is a naturally occurring amino acid selected from Gly, Ser,Thr, Ala, Val, Ile, Lys, Arg, Glu, Asp, Asn, Gln | |
| source | 1..26 | |
| | mol_type = protein | |
| | organism = synthetic construct | |
| SEQUENCE: 13 | | |
| VXTXTXGXGX TXGXAXXXQK AGANGG | | 26 |
| | | |
| SEQ ID NO: 14 | moltype = AA  length = 28 | |
| FEATURE | Location/Qualifiers | |

| | | |
|---|---|---|
| REGION | 1..28 | |
| | note = synthetic construct | |
| SITE | 2 | |
| | note = misc_feature - Xaa is a naturally occurring amino acid selected from Gly, Ser,Thr, Ala, Val, Ile, Lys, Arg, Glu, Asp, Asn, Gln | |
| SITE | 8 | |
| | note = misc_feature - Xaa is a naturally occurring amino acid selected from Gly, Ser,Thr, Ala, Val, Ile, Lys, Arg, Glu, Asp, Asn, Gln | |
| SITE | 12 | |
| | note = misc_feature - Xaa is a naturally occurring amino acid selected from Gly, Ser,Thr, Ala, Val, Ile, Lys, Arg, Glu, Asp, Asn, Gln | |
| SITE | 14 | |
| | note = misc_feature - Xaa is a naturally occurring amino acid selected from Gly, Ser,Thr, Ala, Val, Ile, Lys, Arg, Glu, Asp, Asn, Gln | |
| SITE | 16 | |
| | note = misc_feature - Xaa is a naturally occurring amino acid selected from Gly, Ser,Thr, Ala, Val, Ile, Lys, Arg, Glu, Asp, Asn, Gln | |
| SITE | 18 | |
| | note = misc_feature - Xaa is a naturally occurring amino acid selected from Gly, Ser,Thr, Ala, Val, Ile, Lys, Arg, Glu, Asp, Asn, Gln | |
| SITE | 20 | |
| | note = misc_feature - Xaa is a naturally occurring amino acid selected from Gly, Ser,Thr, Ala, Val, Ile, Lys, Arg, Glu, Asp, Asn, Gln | |
| REGION | 22..24 | |
| | note = misc_feature - Xaa is a naturally occurring amino acid selected from Gly, Ser,Thr, Ala, Val, Ile, Lys, Arg, Glu, Asp, Asn, Gln | |
| SITE | 27 | |
| | note = misc_feature - Xaa is a naturally occurring amino acid selected from Gly, Ser,Thr, Ala, Val, Ile, Lys, Arg, Glu, Asp, Asn, Gln | |
| source | 1..28 | |
| | mol_type = protein | |
| | organism = synthetic construct | |
| SEQUENCE: 14 | | |
| AXSSSGHXAS SXGXGXFXVX NXXXTEXK | | 28 |
| SEQ ID NO: 15 | moltype = AA  length = 24 | |
| FEATURE | Location/Qualifiers | |
| REGION | 1..24 | |
| | note = synthetic construct | |
| SITE | 2 | |
| | note = misc_feature - Xaa is a naturally occurring amino acid selected from Gly, Ser,Thr, Ala, Val, Ile, Lys, Arg, Glu, Asp, Asn, Gln | |
| SITE | 4 | |
| | note = misc_feature - Xaa is a naturally occurring amino acid selected from Gly, Ser,Thr, Ala, Val, Ile, Lys, Arg, Glu, Asp, Asn, Gln | |
| SITE | 6 | |
| | note = misc_feature - Xaa is a naturally occurring amino acid selected from Gly, Ser,Thr, Ala, Val, Ile, Lys, Arg, Glu, Asp, Asn, Gln | |
| SITE | 8 | |
| | note = misc_feature - Xaa is a naturally occurring amino acid selected from Gly, Ser,Thr, Ala, Val, Ile, Lys, Arg, Glu, Asp, Asn, Gln | |
| SITE | 10 | |
| | note = misc_feature - Xaa is a naturally occurring amino acid selected from Gly, Ser,Thr, Ala, Val, Ile, Lys, Arg, Glu, Asp, Asn, Gln | |
| SITE | 12 | |
| | note = misc_feature - Xaa is a naturally occurring amino acid selected from Gly, Ser,Thr, Ala, Val, Ile, Lys, Arg, Glu, Asp, Asn, Gln | |
| REGION | 14..16 | |
| | note = misc_feature - Xaa is a naturally occurring amino acid selected from Gly, Ser,Thr, Ala, Val, Ile, Lys, Arg, Glu, Asp, Asn, Gln | |
| source | 1..24 | |
| | mol_type = protein | |
| | organism = synthetic construct | |

```
SEQUENCE: 15
TXTXGXGXTX GXAXXXQKAG ANGG                                              24

SEQ ID NO: 16           moltype = AA  length = 21
FEATURE                 Location/Qualifiers
REGION                  1..21
                        note = synthetic construct
SITE                    1
                        note = misc_feature - Xaa is a naturally occurring amino
                         acid selected from Gly, Ser,Thr, Ala, Val, Ile, Lys, Arg,
                         Glu, Asp, Asn, Gln
SITE                    8
                        note = misc_feature - Xaa is a naturally occurring amino
                         acid selected from Gly, Ser,Thr, Ala, Val, Ile, Lys, Arg,
                         Glu, Asp, Asn, Gln
SITE                    12
                        note = misc_feature - Xaa is a naturally occurring amino
                         acid selected from Gly, Ser,Thr, Ala, Val, Ile, Lys, Arg,
                         Glu, Asp, Asn, Gln
SITE                    14
                        note = misc_feature - Xaa is a naturally occurring amino
                         acid selected from Gly, Ser,Thr, Ala, Val, Ile, Lys, Arg,
                         Glu, Asp, Asn, Gln
SITE                    16
                        note = misc_feature - Xaa is a naturally occurring amino
                         acid selected from Gly, Ser,Thr, Ala, Val, Ile, Lys, Arg,
                         Glu, Asp, Asn, Gln
SITE                    18
                        note = misc_feature - Xaa is a naturally occurring amino
                         acid selected from Gly, Ser,Thr, Ala, Val, Ile, Lys, Arg,
                         Glu, Asp, Asn, Gln
SITE                    20
                        note = misc_feature - Xaa is a naturally occurring amino
                         acid selected from Gly, Ser,Thr, Ala, Val, Ile, Lys, Arg,
                         Glu, Asp, Asn, Gln
source                  1..21
                        mol_type = protein
                        organism = synthetic construct
SEQUENCE: 16
XTSSSGHXAS SXGXGXFXVX N                                                 21

SEQ ID NO: 17           moltype = AA  length = 38
FEATURE                 Location/Qualifiers
REGION                  1..38
                        note = synthetic construct
SITE                    2
                        note = misc_feature - Xaa is a naturally occurring amino
                         acid selected from Gly, Ser,Thr, Ala, Val, Ile, Lys, Arg,
                         Glu, Asp, Asn, Gln
SITE                    4
                        note = misc_feature - Xaa is a naturally occurring amino
                         acid selected from Gly, Ser,Thr, Ala, Val, Ile, Lys, Arg,
                         Glu, Asp, Asn, Gln
SITE                    6
                        note = misc_feature - Xaa is a naturally occurring amino
                         acid selected from Gly, Ser,Thr, Ala, Val, Ile, Lys, Arg,
                         Glu, Asp, Asn, Gln
SITE                    10
                        note = misc_feature - Xaa is a naturally occurring amino
                         acid selected from Gly, Ser,Thr, Ala, Val, Ile, Lys, Arg,
                         Glu, Asp, Asn, Gln
REGION                  13..14
                        note = misc_feature - Xaa is a naturally occurring amino
                         acid selected from Gly, Ser,Thr, Ala, Val, Ile, Lys, Arg,
                         Glu, Asp, Asn, Gln
SITE                    16
                        note = misc_feature - Xaa is a naturally occurring amino
                         acid selected from Gly, Ser,Thr, Ala, Val, Ile, Lys, Arg,
                         Glu, Asp, Asn, Gln
SITE                    20
                        note = misc_feature - Xaa is a naturally occurring amino
                         acid selected from Gly, Ser,Thr, Ala, Val, Ile, Lys, Arg,
                         Glu, Asp, Asn, Gln
SITE                    23
                        note = misc_feature - Xaa is a naturally occurring amino
                         acid selected from Gly, Ser,Thr, Ala, Val, Ile, Lys, Arg,
                         Glu, Asp, Asn, Gln
REGION                  25..27
                        note = misc_feature - Xaa is a naturally occurring amino
```

-continued

|  |  |
|---|---|
| SITE | acid selected from Gly, Ser,Thr, Ala, Val, Ile, Lys, Arg, Glu, Asp, Asn, Gln<br>35<br>note = misc_feature - Xaa is a naturally occurring amino acid selected from Gly, Ser,Thr, Ala, Val, Ile, Lys, Arg, Glu, Asp, Asn, Gln |
| SITE | 37<br>note = misc_feature - Xaa is a naturally occurring amino acid selected from Gly, Ser,Thr, Ala, Val, Ile, Lys, Arg, Glu, Asp, Asn, Gln |
| source | 1..38<br>mol_type = protein<br>organism = synthetic construct |

SEQUENCE: 17
QXGXTXGGAX VSXXGXTQGX GSXDXXXDGG GGDKXRXK                                38

| SEQ ID NO: 18 | moltype = AA   length = 33 |
|---|---|
| FEATURE | Location/Qualifiers |
| REGION | 1..33<br>note = synthetic construct |
| SITE | 10<br>note = misc_feature - Xaa is a naturally occurring amino acid selected from Gly, Ser,Thr, Ala, Val, Ile, Lys, Arg, Glu, Asp, Asn, Gln |
| SITE | 12<br>note = misc_feature - Xaa is a naturally occurring amino acid selected from Gly, Ser,Thr, Ala, Val, Ile, Lys, Arg, Glu, Asp, Asn, Gln |
| SITE | 14<br>note = misc_feature - Xaa is a naturally occurring amino acid selected from Gly, Ser,Thr, Ala, Val, Ile, Lys, Arg, Glu, Asp, Asn, Gln |
| SITE | 16<br>note = misc_feature - Xaa is a naturally occurring amino acid selected from Gly, Ser,Thr, Ala, Val, Ile, Lys, Arg, Glu, Asp, Asn, Gln |
| SITE | 18<br>note = misc_feature - Xaa is a naturally occurring amino acid selected from Gly, Ser,Thr, Ala, Val, Ile, Lys, Arg, Glu, Asp, Asn, Gln |
| SITE | 20<br>note = misc_feature - Xaa is a naturally occurring amino acid selected from Gly, Ser,Thr, Ala, Val, Ile, Lys, Arg, Glu, Asp, Asn, Gln |
| REGION | 22..23<br>note = misc_feature - Xaa is a naturally occurring amino acid selected from Gly, Ser,Thr, Ala, Val, Ile, Lys, Arg, Glu, Asp, Asn, Gln |
| REGION | 25..27<br>note = misc_feature - Xaa is a naturally occurring amino acid selected from Gly, Ser,Thr, Ala, Val, Ile, Lys, Arg, Glu, Asp, Asn, Gln |
| REGION | 29..30<br>note = misc_feature - Xaa is a naturally occurring amino acid selected from Gly, Ser,Thr, Ala, Val, Ile, Lys, Arg, Glu, Asp, Asn, Gln |
| SITE | 33<br>note = misc_feature - Xaa is a naturally occurring amino acid selected from Gly, Ser,Thr, Ala, Val, Ile, Lys, Arg, Glu, Asp, Asn, Gln |
| source | 1..33<br>mol_type = protein<br>organism = synthetic construct |

SEQUENCE: 18
AVGNSGVSGX GXSXGXGXFX QXXEXXXKXX KRX                                     33

| SEQ ID NO: 19 | moltype = AA   length = 50 |
|---|---|
| FEATURE | Location/Qualifiers |
| REGION | 1..50<br>note = synthetic construct |
| SITE | 2<br>note = misc_feature - Xaa is a naturally occurring amino acid selected from Gly, Ser,Thr, Ala, Val, Ile, Lys, Arg, Glu, Asp, Asn, Gln |
| SITE | 4<br>note = misc_feature - Xaa is a naturally occurring amino acid selected from Gly, Ser,Thr, Ala, Val, Ile, Lys, Arg, Glu, Asp, Asn, Gln |
| SITE | 6 |

```
                   note = misc_feature - Xaa is a naturally occurring amino
                    acid selected from Gly, Ser,Thr, Ala, Val, Ile, Lys, Arg,
                    Glu, Asp, Asn, Gln
SITE               8
                   note = misc_feature - Xaa is a naturally occurring amino
                    acid selected from Gly, Ser,Thr, Ala, Val, Ile, Lys, Arg,
                    Glu, Asp, Asn, Gln
SITE               10
                   note = misc_feature - Xaa is a naturally occurring amino
                    acid selected from Gly, Ser,Thr, Ala, Val, Ile, Lys, Arg,
                    Glu, Asp, Asn, Gln
SITE               12
                   note = misc_feature - Xaa is a naturally occurring amino
                    acid selected from Gly, Ser,Thr, Ala, Val, Ile, Lys, Arg,
                    Glu, Asp, Asn, Gln
SITE               14
                   note = misc_feature - Xaa can be any naturally occurring
                    amino acid
REGION             16..18
                   note = misc_feature - Xaa is a naturally occurring amino
                    acid selected from Gly, Ser,Thr, Ala, Val, Ile, Lys, Arg,
                    Glu, Asp, Asn, Gln
REGION             27..28
                   note = misc_feature - Xaa is a naturally occurring amino
                    acid selected from Gly, Ser,Thr, Ala, Val, Ile, Lys, Arg,
                    Glu, Asp, Asn, Gln
SITE               30
                   note = misc_feature - Xaa is a naturally occurring amino
                    acid selected from Gly, Ser,Thr, Ala, Val, Ile, Lys, Arg,
                    Glu, Asp, Asn, Gln
REGION             32..33
                   note = misc_feature - Xaa is a naturally occurring amino
                    acid selected from Gly, Ser,Thr, Ala, Val, Ile, Lys, Arg,
                    Glu, Asp, Asn, Gln
REGION             35..36
                   note = misc_feature - Xaa is a naturally occurring amino
                    acid selected from Gly, Ser,Thr, Ala, Val, Ile, Lys, Arg,
                    Glu, Asp, Asn, Gln
SITE               38
                   note = misc_feature - Xaa is a naturally occurring amino
                    acid selected from Gly, Ser,Thr, Ala, Val, Ile, Lys, Arg,
                    Glu, Asp, Asn, Gln
SITE               40
                   note = misc_feature - Xaa is a naturally occurring amino
                    acid selected from Gly, Ser,Thr, Ala, Val, Ile, Lys, Arg,
                    Glu, Asp, Asn, Gln
REGION             42..44
                   note = misc_feature - Xaa is a naturally occurring amino
                    acid selected from Gly, Ser,Thr, Ala, Val, Ile, Lys, Arg,
                    Glu, Asp, Asn, Gln
SITE               46
                   note = misc_feature - Xaa is a naturally occurring amino
                    acid selected from Gly, Ser,Thr, Ala, Val, Ile, Lys, Arg,
                    Glu, Asp, Asn, Gln
SITE               49
                   note = misc_feature - Xaa is a naturally occurring amino
                    acid selected from Gly, Ser,Thr, Ala, Val, Ile, Lys, Arg,
                    Glu, Asp, Asn, Gln
source             1..50
                   mol_type = protein
                   organism = synthetic construct
SEQUENCE: 19
VXTXTXGXGX TXGXAXXXQK AGANGGXXRX EXXKXXEXDX KXXXKXEKXD                 50

SEQ ID NO: 20      moltype = AA  length = 42
FEATURE            Location/Qualifiers
REGION             1..42
                   note = synthetic construct
SITE               2
                   note = misc_feature - Xaa is a naturally occurring amino
                    acid selected from Gly, Ser,Thr, Ala, Val, Ile, Lys, Arg,
                    Glu, Asp, Asn, Gln
SITE               8
                   note = misc_feature - Xaa is a naturally occurring amino
                    acid selected from Gly, Ser,Thr, Ala, Val, Ile, Lys, Arg,
                    Glu, Asp, Asn, Gln
SITE               12
                   note = misc_feature - Xaa is a naturally occurring amino
                    acid selected from Gly, Ser,Thr, Ala, Val, Ile, Lys, Arg,
```

```
                        Glu, Asp, Asn, Gln
SITE                    14
                        note = misc_feature - Xaa is a naturally occurring amino
                         acid selected from Gly, Ser,Thr, Ala, Val, Ile, Lys, Arg,
                         Glu, Asp, Asn, Gln
SITE                    16
                        note = misc_feature - Xaa is a naturally occurring amino
                         acid selected from Gly, Ser,Thr, Ala, Val, Ile, Lys, Arg,
                         Glu, Asp, Asn, Gln
SITE                    18
                        note = misc_feature - Xaa is a naturally occurring amino
                         acid selected from Gly, Ser,Thr, Ala, Val, Ile, Lys, Arg,
                         Glu, Asp, Asn, Gln
SITE                    20
                        note = misc_feature - Xaa is a naturally occurring amino
                         acid selected from Gly, Ser,Thr, Ala, Val, Ile, Lys, Arg,
                         Glu, Asp, Asn, Gln
REGION                  22..24
                        note = misc_feature - Xaa is a naturally occurring amino
                         acid selected from Gly, Ser,Thr, Ala, Val, Ile, Lys, Arg,
                         Glu, Asp, Asn, Gln
SITE                    27
                        note = misc_feature - Xaa is a naturally occurring amino
                         acid selected from Gly, Ser,Thr, Ala, Val, Ile, Lys, Arg,
                         Glu, Asp, Asn, Gln
REGION                  30..32
                        note = misc_feature - Xaa is a naturally occurring amino
                         acid selected from Gly, Ser,Thr, Ala, Val, Ile, Lys, Arg,
                         Glu, Asp, Asn, Gln
SITE                    34
                        note = misc_feature - Xaa is a naturally occurring amino
                         acid selected from Gly, Ser,Thr, Ala, Val, Ile, Lys, Arg,
                         Glu, Asp, Asn, Gln
REGION                  36..39
                        note = misc_feature - Xaa is a naturally occurring amino
                         acid selected from Gly, Ser,Thr, Ala, Val, Ile, Lys, Arg,
                         Glu, Asp, Asn, Gln
SITE                    41
                        note = misc_feature - Xaa is a naturally occurring amino
                         acid selected from Gly, Ser,Thr, Ala, Val, Ile, Lys, Arg,
                         Glu, Asp, Asn, Gln
source                  1..42
                        mol_type = protein
                        organism = synthetic construct
SEQUENCE: 20
AXSSSGHXAS SXGXGXFXVX NXXXTEXKEX XXEXKXXXXE XD                              42

SEQ ID NO: 21           moltype = AA   length = 38
FEATURE                 Location/Qualifiers
REGION                  1..38
                        note = synthetic construct
source                  1..38
                        mol_type = protein
                        organism = synthetic construct
SEQUENCE: 21
QAGATAGGAA VSAAGATQGA GSADAAADGG GGDKARAK                                   38

SEQ ID NO: 22           moltype = AA   length = 38
FEATURE                 Location/Qualifiers
REGION                  1..38
                        note = synthetic construct
source                  1..38
                        mol_type = protein
                        organism = synthetic construct
SEQUENCE: 22
QSGSTSGGAS VSSSGSTQGS GSSDSSSDGG GGDKSRSK                                   38

SEQ ID NO: 23           moltype = AA   length = 38
FEATURE                 Location/Qualifiers
REGION                  1..38
                        note = synthetic construct
source                  1..38
                        mol_type = protein
                        organism = synthetic construct
SEQUENCE: 23
QGGGTGGGAG VSGGGGTQGG GSGDGGGDGG GGDKGRGK                                   38

SEQ ID NO: 24           moltype = AA   length = 38
FEATURE                 Location/Qualifiers
```

```
REGION                    1..38
                          note = synthetic construct
source                    1..38
                          mol_type = protein
                          organism = synthetic construct
SEQUENCE: 24
QTGTTTGGAT VSTTGTTQGT GSTDTTTDGG GGDKTRTK                          38

SEQ ID NO: 25             moltype = AA  length = 33
FEATURE                   Location/Qualifiers
REGION                    1..33
                          note = synthetic construct
source                    1..33
                          mol_type = protein
                          organism = synthetic construct
SEQUENCE: 25
AVGNSGVSGA GASAGAGAFA QAAEAAAKAA KRA                               33

SEQ ID NO: 26             moltype = AA  length = 33
FEATURE                   Location/Qualifiers
REGION                    1..33
                          note = synthetic construct
source                    1..33
                          mol_type = protein
                          organism = synthetic construct
SEQUENCE: 26
AVGNSGVSGS GSSSGSGSFS QSSESSSKSS KRS                               33

SEQ ID NO: 27             moltype = AA  length = 33
FEATURE                   Location/Qualifiers
REGION                    1..33
                          note = synthetic construct
source                    1..33
                          mol_type = protein
                          organism = synthetic construct
SEQUENCE: 27
AVGNSGVSGG GGSGGGGGFG QGGEGGGKGG KRG                               33

SEQ ID NO: 28             moltype = AA  length = 33
FEATURE                   Location/Qualifiers
REGION                    1..33
                          note = synthetic construct
source                    1..33
                          mol_type = protein
                          organism = synthetic construct
SEQUENCE: 28
AVGNSGVSGT GTSTGTGTFT QTTETTTKTT KRT                               33

SEQ ID NO: 29             moltype = AA  length = 50
FEATURE                   Location/Qualifiers
REGION                    1..50
                          note = synthetic construct
source                    1..50
                          mol_type = protein
                          organism = synthetic construct
SEQUENCE: 29
VATATAGAGA TAGAAAAAQK AGANGGAARA EAAKAAEADA KAAAKAEKAD             50

SEQ ID NO: 30             moltype = AA  length = 50
FEATURE                   Location/Qualifiers
REGION                    1..50
                          note = synthetic construct
source                    1..50
                          mol_type = protein
                          organism = synthetic construct
SEQUENCE: 30
VSTSTSGSGS TSGSASSSQK AGANGGSSRS ESSKSSESDS KSSSKSEKSD             50

SEQ ID NO: 31             moltype = AA  length = 50
FEATURE                   Location/Qualifiers
REGION                    1..50
                          note = synthetic construct
source                    1..50
                          mol_type = protein
                          organism = synthetic construct
SEQUENCE: 31
VGTGTGGGGG TGGGAGGGQK AGANGGGGRG EGGKGGEGDG KGGGKGEKGD             50

SEQ ID NO: 32             moltype = AA  length = 50
```

```
FEATURE                 Location/Qualifiers
REGION                  1..50
                        note = synthetic construct
source                  1..50
                        mol_type = protein
                        organism = synthetic construct
SEQUENCE: 32
VTTTTTGTGT TTGTATTTQK AGANGGTTRT ETTKTTETDT KTTTKTEKTD                50

SEQ ID NO: 33           moltype = AA  length = 42
FEATURE                 Location/Qualifiers
REGION                  1..42
                        note = synthetic construct
source                  1..42
                        mol_type = protein
                        organism = synthetic construct
SEQUENCE: 33
AASSSGHAAS SAGAGAFAVA NAAATEAKEA AAEAKAAAAE AD                        42

SEQ ID NO: 34           moltype = AA  length = 42
FEATURE                 Location/Qualifiers
REGION                  1..42
                        note = synthetic construct
source                  1..42
                        mol_type = protein
                        organism = synthetic construct
SEQUENCE: 34
ASSSSGHSAS SSGSGSFSVS NSSSTESKES SSESKSSSSE SD                        42

SEQ ID NO: 35           moltype = AA  length = 42
FEATURE                 Location/Qualifiers
REGION                  1..42
                        note = synthetic construct
source                  1..42
                        mol_type = protein
                        organism = synthetic construct
SEQUENCE: 35
AGSSSGHGAS SGGGGGFGVG NGGGTEGKEG GGEGKGGGGE GD                        42

SEQ ID NO: 36           moltype = AA  length = 42
FEATURE                 Location/Qualifiers
REGION                  1..42
                        note = synthetic construct
source                  1..42
                        mol_type = protein
                        organism = synthetic construct
SEQUENCE: 36
ATSSSGHTAS STGTGTFTVT NTTTTETKET TTETKTTTTE TD                        42
```